US 6,569,993 B1

(12) United States Patent
Sledeski et al.

(10) Patent No.: US 6,569,993 B1
(45) Date of Patent: May 27, 2003

(54) PROCESS FOR THE PREPARATION OF RESIN-BOUND CYCLIC PEPTIDES

(75) Inventors: Adam W. Sledeski, Collegeville, PA (US); James J. Mencel, Lansdale, PA (US)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/442,989

(22) Filed: Nov. 18, 1999

Related U.S. Application Data

(63) Continuation of application No. PCT/US99/08435, filed on Apr. 15, 1999.
(60) Provisional application No. 60/081,897, filed on Apr. 15, 1998, now abandoned.

(51) Int. Cl.[7] ................................................. C07K 1/04
(52) U.S. Cl. ....................... 530/333; 530/317; 530/324; 530/328; 530/330; 514/17; 514/18; 514/19; 514/11; 514/12; 514/14
(58) Field of Search ................................ 530/333, 334, 530/339, 345, 317, 328, 330, 324; 514/17–19, 11, 12, 14

(56) References Cited

U.S. PATENT DOCUMENTS

| | | | | | |
|---|---|---|---|---|---|
| 4,959,352 A | * | 9/1990 | Felix | .............................. | 514/9 |
| 5,049,654 A | * | 9/1991 | Morita | .......................... | 530/307 |
| 5,064,939 A | * | 11/1991 | Rivier | ........................... | 530/317 |
| 5,169,862 A | * | 12/1992 | Burke | .......................... | 514/450 |
| 5,508,382 A | | 4/1996 | Ohsaki et al. | ............... | 530/307 |
| 5,556,940 A | * | 9/1996 | Willick | .......................... | 530/317 |
| 5,569,742 A | | 10/1996 | Kirby et al. | ................. | 530/317 |
| 5,674,839 A | | 10/1997 | Hruby et al. | ................... | 514/9 |
| 5,939,383 A | * | 8/1999 | Remacle | .......................... | 514/9 |
| 6,008,058 A | * | 12/1999 | Spatola | .......................... | 436/518 |
| 6,034,057 A | * | 3/2000 | Dutta | .............................. | 514/9 |
| 6,169,071 B1 | * | 1/2001 | Blaschuk | .......................... | 514/4 |
| 6,183,722 B1 | * | 2/2001 | Dean et al. | ................. | 424/1.69 |
| 6,184,345 B1 | * | 2/2001 | Reissmann | ................... | 530/323 |

FOREIGN PATENT DOCUMENTS

| | | | |
|---|---|---|---|
| GB | 2282813 | * | 4/1995 |
| JP | 6-21079 | | 2/1994 |
| WO | 96/40193 | * | 12/1996 |
| WO | 9851324 | | 11/1998 |
| WO | 98/51324 | * | 11/1998 |
| WO | 9952933 | | 10/1999 |

* cited by examiner

Primary Examiner—Christopher S. F. Low
Assistant Examiner—David Lukton
(74) Attorney, Agent, or Firm—Irving Newman

(57) ABSTRACT

This invention is directed to a process for the solid phase, fragment-based synthesis of resin-bound cyclic peptide analogs of parathyroid hormones and analogs of parathyroid hormone-related proteins, which analogs contain at least one bridge between the side chains of two non-adjacent amino acid residues, and to peptide fragments useful therefor.

7 Claims, No Drawings

PROCESS FOR THE PREPARATION OF RESIN-BOUND CYCLIC PEPTIDES

CROSS-REFERENCE TO RELATED APPLICATIONS

This application is a continuation of International Application No. PCT/US99/08435, filed Apr. 15, 1999, which application is, in turn, a continuation-in-part of U.S. Provisional Application No. 60/081,897, filed Apr. 15, 1998, now abandoned.

FIELD OF THE INVENTION

This invention is directed to a process for the fragment-based preparation of resin-bound cyclic peptide analogs of parathyroid hormones and analogs of parathyroid hormone-related proteins, which analogs contain at least one bridge between the side chains of two non-adjacent amino acid residues. More particularly, the invention is directed to a process for the solid-phase synthesis of such cyclic peptide analogs, and to peptide fragments useful therefor.

BACKGROUND OF THE INVENTION

Cyclic peptide subunits are present in a wide variety of peptides possessing useful biological activity, including parathyroid hormone analogs and parathyroid hormone-related protein analogs, vasoactive peptide analogs, cholecystokinin analogs, tumor necrosis factor (TNF) derived peptides, calcitonin analogs, somatostatin analogs, cell adhesion modulators, growth hormone releasing factor (GRF) analogs, bradykinin antagonists, analogs of tyrosine activation motifs (TAM Mimics) and amylin agonists. Of particular interest are the cyclic peptide parathyroid hormone (hPTH) analogs and parathyroid hormone-related protein (hPTHrP) analogs.

Human parathyroid hormone (hPTH) is an 84 amino acid protein which is a major regulator of calcium homeostasis. Parathyroid hormone-related protein (hPTHrP) is a 139 to 171 amino acid protein with N-terminal homology to hPTH. The N-terminal fragments of hPTH and hPTHrP, particularly those consisting of amino acids 1–34, retain the full biological activity of the parent hormone.

hPTH(1–34) has the following amino acid sequence:
Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe. (SEQ ID NO: 26)

hPTHrP(1–34) has the following amino acid sequence:
Ala-Val-Ser-Glu-His-Gln-Leu-Leu-His-Asp-Lys-Gly-Lys-Ser-Ile-Gln-Asp-Leu-Arg-Arg-Arg-Phe-Phe-Leu-His-His-Leu-Ile-Ala-Glu-Ile-His-Thr-Ala. (SEQ ID NO: 27)

The biological activity of hPTH is reflected in the activation of two secondary messenger systems: G-protein coupled adenylyl cyclase (AC) and G-protein coupled and uncoupled protein kinase C (PKC) activity. The N-terminal fragments hPTH(1–34)OH and hPTH(1–31)NH2 have been demonstrated to be anabolic with respect to bone formation in humans and ovariectomized rats, respectively. This increase in bone growth has been demonstrated to be coupled with stimulation of adenylyl cyclase activity. Analogs of these N-terminal fragments have significant therapeutic potential for the treatment of physiological conditions associated with bone cell calcium regulation including hypocalcemia; osteoporosis; osteopenia; and disorders associated with osteoporosis and osteopenia such as hyperparathyroidism, hypoparathyroidism, and Cushings syndrome; glucocorticoid- and immunosuppressant-induced osteopacnia; and bone fracture and bone refracture repair.

It has also been established that deletion of up to six amino acid residues from the N-terminus of hPTH(1–34) markedly decreases the resulting analog's ability to stimulate adenylyl cyclase while having little effect on receptor binding. Thus, analogs of hPTH(1–34) truncated by up to six amino acid residues at the N-teminus inhibit the action of PTH and are useful in the treatment of disorders characterized by an excess of PTH such as hyperparathyrodism and hyperparathyrodism-related hypercalcemia crisis, hypercalcemia of malignancy, renal failure and hypertension.

Acyclic analogs of hPTH(1–27) to (1–34) are disclosed in U.S. Pat. No. 4,086,196. Acyclic analogs of hPTH(1–34) and hPTHrP(1–34) are disclosed in U.S. Pat. No. 5,589,452. [Nle$^8$, Nle$^{18}$, Tyr$^{34}$, or Phe$^{34}$]hPTH(1–34) are disclosed in U.S. Pat. No. 4,656,250. [Nle$^8$, Nle$^{18}$, Tyr$^{34}$]hPTH(1–34) and N-truncated derivatives thereof are disclosed in U.S. Pat. Nos. 4,771,124 and 4,423,037. Other acyclic analogs of PTH(1–34) are disclosed in U.S. Pat. Nos. 5,723,577 and 5,434,246, WO 97/02834, EPA 561 412-A1, EPA 747 817-A2, WO-94/02510, WO9603437, and WO9511988-A1. Analogs of hPTH(1–28)NH$_2$ to hPTH(1–31)NH$_2$ and [Leu$^{27}$]hPTH(1–28)NH$_2$ to [Leu$^{27}$]hPTH(1–33)NH$_2$ are decribed in U.S. Pat. No. 5,556,940. Acyclic antagonists of the PTH receptor including N-terminally-truncated analogs of PTH are disclosed in U.S. Pat. Nos. 5,446,130, 5,229,489, 4,771,124 and 4,423,037.

Cyclic and bicyclic analogs of hPTH and hPTHrP have been disclosed. Cyclo(Lys$^{26}$-Asp$^{30}$)[Leu$^{27}$]hPTH(1–34)NH$_2$ and cyclo(Lys$^{27}$-Asp$^{30}$)hPTH(1–34)NH$_2$ are disclosed in U.S. Pat. No. 5,556,940. Cyclo(Lys$^{26}$-Asp$^{30}$)[Leu$^{27}$]hPTH(1–31)NH$_2$, cyclo(Glu$^{22}$-Lys$^{26}$)[Leu$^{27}$]hPTH(1–31)NH$_2$, and cyclo(Lys$^{27}$-Asp$^{30}$)hPTH(1–31)NH$_2$ are decribed by Barbier, et al., *J. Med. Chem.* 1997, 40, 1373. Monocyclic and bicyclic derivatives of hPTH(1–34) or hPTHrP(1–34) are disclosed in patent documents WO 96/40193, DE19508672-A1, and by A. Bisello, et al., in *Biochemistry* 1997, 36, 3293. Cyclo(Lys$^{13}$-Asp$^{17}$)hPTHrP(7–34)NH$_2$, a potent antagonist of the PTH receptor, is disclosed by M. Chorev, et al., *Biochemistry* 1991, 30, 5698. Also, Kanmera, et al., has described a series of amide-containing analogs of hPTHrP, *Peptide Chemistry* 1993: Okada, Y., ed.; Protein Research Foundation, Osaka, 1994, 321–324." WO 98/51324 discloses cyclic peptide compounds of formula I

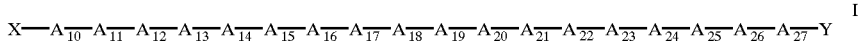

I and pharmaceutically acceptable salts and prodrugs thereof wherein

X is selected from the group consisting of (a) $R_{1a}$—$A_0$—$A_1$—$A_2$—$A_3$—$A_4$—$A_5$—$A_6$—$A_7$—$A_8$—$A_9$—, (b) $R_{1a}$—$A_2$—$A_3$—$A_4$—$A_5$—$A_6$—$A_7$—$A_8$—$A_9$—, (c) $R_{1b}$—$A_3$—$A_4$—$A_5$—$A_6$—$A_7$—$A_8$—$A_9$—, (d) $R_{1a}$—$A_4$—$A_5$—$A_6$—$A_7$—$A_8$—$A_9$—, (e) $R_{1a}$—$A_5$—$A_6$—$A_7$—$A_8$—$A_9$—, (f) $R_{1a}$—$A_6$—$A_7$—$A_8$—$A_9$—,
(g) $R_{1a}$—$A_7$—$A_8$—$A_9$—,
(h) $R_{1a}$—$A_8$—$A_9$—,
(i) $R_{1a}$—$A_9$—, and
(j) $R_{1a}$—;

Y is selected from the group consisting of
(a) —$R_3$,
(b) —$A_{28}$—$R_3$,
(c) —$A_{28}$—$A_{29}$—$R_3$,
(d) —$A_{28}$—$A_{29}$—$A_{30}$—$R_3$,
(e) —$A_{28}$—$A_{29}$—$A_{30}$—$A_{31}$—$R_3$,
(e) —$A_{28}$—$A_{29}$—$A_{30}$—$A_{31}$—$A_{32}$—$R_3$,
(g) —$A_{28}$—$A_{29}$—$A_{30}$—$A_{31}$—$A_{32}$—$A_{33}$—$R_3$, and
(h) —$A_{28}$—$A_{29}$—$A_{30}$—$A_{31}$—$A_{32}$—$A_{33}$—$A_{34}$—$R_3$;

$R_{1a}$ is H, alkyl, aralkyl or —$COR_2$;
$R_{1b}$ is $R_{1a}$ or a group of formula

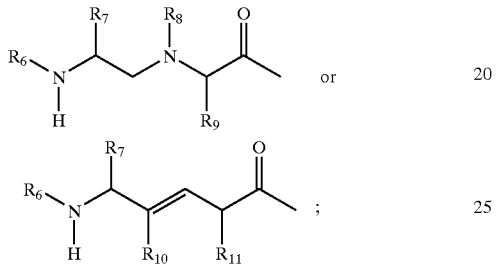

or ;

$R_2$ is alkyl, alkenyl, alkynyl, aryl or aralkyl;
$R_3$ is a group of formula $A_{35}$—$OR_4$ or $A_{35}$—$NR_4R_5$;
$R_4$ and $R_5$ are independently H or lower alkyl;
$R_6$ and $R_9$ are independently H or alkyl;
$R_7$ is alkyl;
$R_8$ is H, alkyl or $COR_2$;
$R_{10}$ is H or halogen;
$R_{11}$ is alkyl or aralkyl;
m is 1, 2 or 3;
n is 3 or 4;
$A_0$ is absent or a peptide of from one to six amino acid residues;
$A_1$ is Ser, Ala, Gly or D-Pro, or an equivalent amino acid thereof;
$A_2$ is Ala, Val or Gly, or an equivalent amino acid thereof;
$A_3$ is Ala, Ser, Gly or D-Pro, or an equivalent amino acid thereof;
$A_4$ is Glu, Ala or Gly, or an equivalent amino acid thereof,
$A_5$ is Ile, His, Ala or Gly, or an equivalent amino acid thereof;
$A_6$ is Ala, Gln, Gly or D-Pro, or an equivalent amino acid thereof;
$A_7$ is Ala, Leu, Gly, or an equivalent amino acid thereof;
$A_8$ is Leu, Nle, Gly or D-Pro, or an equivalent amino acid thereof;
$A_9$ is His, Ala, D-Pro or Gly, or an equivalent amino acid thereof;
$A_{10}$ is Ala, Asn, Asp, Cys, homo-Cys, Glu, Gly, Lys, Orn, Ser, Thr, D-Pro, —NHCH[$(CH_2)_m NH_2$]CO— or —NHCH[$(CH_2)_n CO_2H$]CO—;
$A_{11}$ is Ala, Gly, Leu or Lys, or an equivalent amino acid thereof;
$A_{12}$ is Ala or Gly, or an equivalent amino acid thereof;
$A_{13}$ is Ala, Asn, Asp, Cys, homo-Cys, Glu, Gly, Lys, Orn, Ser, Thr, —NHCH[$(CH_2)_m NH_2$]CO— or —NHCH[$(CH_2)_n CO_2H$]CO—;
$A_{14}$ is Ala, Asn, Asp, Cys, homo-Cys, Glu, Gly, His, Lys, Orn, Ser, Thr, D-Pro, —NHCH[$(CH_2)_m NH_2$]CO— or —NHCH[$(CH_2)_n CO_2H$]CO—;
$A_{15}$ is Ala, Gly, Ile, D-Pro or Leu, or an equivalent amino acid thereof;
$A_{16}$ is Asn, Ala, Gly, D-Pro or Gln, or an equivalent amino acid thereof;
$A_{17}$ is Ala, Asn, Asp, Cys, homo-Cys, Glu, Gly, Lys, Orn, Ser, Thr, D-Pro, —NHCH[$(CH_2)_m NH_2$]CO— or —NHCH[$(CH_2)_n CO_2H$]CO—;
$A_{18}$ is Asp, Cys, homo-Cys, Glu, His, Leu, Lys, Orn, Nle, Ser, Thr, —NHCH[$(CH_2)_m NH_2$]CO— or —NHCH[$(CH_2)_n CO_2H$]CO—;
$A_{19}$ is Arg or Glu, or an equivalent amino acid thereof;
$A_{20}$ is Arg or an equivalent amino acid thereof;
$A_{21}$ is Arg, Asp, Cys, homo-Cys, Glu, Lys, Orn, Ser, Thr, Val, —NHCH[$(CH_2)_m NH_2$]CO— or —NHCH[$(CH_2)_n CO_2H$]CO—;
$A_{22}$ is Asp, Cys, homo-Cys, Glu, His, Lys, Orn, Phe, Ser, Thr, —NHCH[$(CH_2)_m NH_2$]CO— or —NHCH[$(CH_2)_n CO_2H$]CO—;
$A_{23}$ is Leu, Phe or Trp, or an equivalent amino acid thereof;
$A_{24}$ is Leu or an equivalent amino acid thereof;
$A_{25}$ is Arg, Asp, Cys, homo-Cys, Glu, His, Lys, Orn, D-Pro, Ser, Thr, —NHCH[$(CH_2)_m NH_2$]CO— or —NHCH[$(CH_2)_n CO_2H$]CO—;
$A_{26}$ is Asp, Cys, homo-Cys, Glu, His, Lys, Orn, Ser, Thr, —NHCH[$(CH_2)_m NH_2$]CO— or —NHCH[$(CH_2)_n CO_2H$]CO—;
$A_{27}$ is Leu or Lys, or an equivalent amino acid thereof;
$A_{28}$ is Ile or Leu, or an equivalent amino acid thereof;
$A_{29}$ is Ala, Asp, Cys, homo-Cys, Glu, Gln, Lys, Orn, Ser, Thr, —NHCH[$(CH_2)_m NH_2$]CO— or —NHCH[$(CH_2)_n CO_2H$]CO—;
$A_{30}$ is Asp, Cys, homo-Cys, Glu, Gly, Lys, Orn, Ser, Thr, —NHCH[$(CH_2)_m NH_2$]CO— or —NHCH[$(CH_2)_n CO_2H$]CO—;
$A_{31}$ is Ile, Leu or Val, or an equivalent amino acid thereof;
$A_{32}$ is His, or an equivalent amino acid thereof;
$A_{33}$ is Asn or Thr, or an equivalent amino acid thereof; and
$A_{34}$ is Ala or Phe, or an equivalent amino acid thereof;
$A_{35}$ is absent or a peptide of from 1 to 4 amino acids; and
the side chains of at least one of the following pairs of amino acid residues, $A_{10}$ and $A_{14}$, $A_{13}$ and $A_{17}$, $A_{14}$ and $A_{18}$, $A_{17}$ and $A_{21}$, $A_{18}$ and $A_{22}$, $A_{21}$ and $A_{25}$, $A_{25}$ and $A_{29}$ and $A_{26}$ and $A_{30}$ are linked through an amide, ester, disulfide or lanthionine bond to form a bridge, and the side chain of each of the following amino acid residues, $A_{10}$, $A_{13}$, $A_{14}$, $A_{17}$, $A_{18}$, $A_{21}$, $A_{22}$, $A_{25}$, $A_{26}$, $A_{29}$, and $A_{30}$. contributes, at most, to the formation of a single bridge; provided that when the side chains of the following pairs of amino acid residues, $A_{13}$ and $A_{17}$ or $A_{26}$ and $A_{30}$ are linked through an amide, disulfide or lanthionine bond to form a bridge, then the side chains of at least one of the following pairs of amino acid residues, $A_{10}$ and $A_{14}$, $A_{14}$ and $A_{18}$, $A_{17}$ and $A_{21}$, $A_{18}$ and $A_{22}$, $A_{21}$ and $A_{25}$ and $A_{25}$ and $A_{29}$ are also linked through an amide, ester, disulfide or lanthionine bond.

A preferred subset of the peptide compounds of formula I comprises the peptide compounds wherein
X is selected from the group consisting of
(a) $R_{1a}-A_0-A_1-A_2-A_3-A_4-A_5-A_6-A_7-A_8-A_9-$,
(b) $R_{1a}-A_2-A_3-A_4-A_5-A_6-A_7-A_8-A_9-$,
(c) $R_{1b}-A_3-A_4-A_5-A_6-A_7-A_8-A_9-$,
(d) $R_{1a}-A_4-A_5-A_6-A_7-A_8-A_9-$,
(e) $R_{1a}-A_5-A_6-A_7-A_8-A_9-$,
(f) $R_{1a}-A_6-A_7-A_8-A_9-$,
(g) $R_{1a}-A_7-A_8-A_9-$,
(h) $R_{1a}-A_8-A_9-$,
(i) $R_{1a}-A_9-$, and
(j) $R_{1a}-$;

Y is selected from the group consisting of
(a) $-R_3$,
(b) $-A_{28}-R_3$,
(c) $-A_{28}-A_{29}-R_3$,
(d) $-A_{28}-A_{29}-A_{30}-R_3$,
(e) $-A_{28}-A_{29}-A_{30}-A_{31}-R_3$,
(f) $-A_{28}-A_{29}-A_{30}-A_{31}-A_{32}-R_3$,
(g) $-A_{28}-A_{29}-A_{30}-A_{31}-A_{32}-A_{33}-R_3$, and
(h) $-A_{28}-A_{29}-A_{30}-A_{31}-A_{32}-A_{33}-A_{34}-R_3$;

$R_{1a}$ is H, alkyl, aralkyl or $-COR_2$;
$R_{1b}$ is $R_{1a}$ or a group of formula

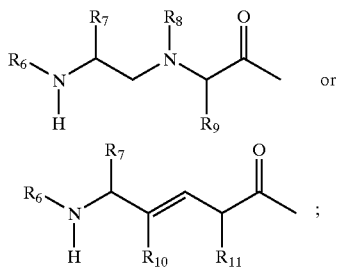

$R_2$ is alkyl, alkenyl, alkynyl, aryl or aralkyl;
$R_3$ is a group of formula $A_{35}-OR_4$ or $A_{35}-NR_4R_5$;
$R_4$ and $R_5$ are independently H or lower alkyl;
$R_6$ and $R_9$ are independently H or alkyl;
$R_7$ is alkyl;
$R_8$ is H, alkyl or $COR_2$;
$R_{10}$ is H or halogen;
$R_{11}$ is alkyl or aralkyl;
$A_0$ is absent or a peptide of from one to six amino acid residues;
$A_1$ is Ser, Ala, Gly or D-Pro, or an equivalent amino acid thereof;
$A_2$ is Ala, Val or Gly, or an equivalent amino acid thereof;
$A_3$ is Ala, Ser, Gly or D-Pro, or an equivalent amino acid thereof;
$A_4$ is Glu, Ala or Gly, or an equivalent amino acid thereof;
$A_5$ is Ile, His, Ala or Gly, or an equivalent amino acid thereof;
$A_6$ is Ala, Gln, Gly or D-Pro, or an equivalent amino acid thereof,
$A_7$ is Ala, Leu or Gly, or an equivalent amino acid thereof;
$A_8$ is Leu, Nle, Gly or D-Pro, or an equivalent amino acid thereof;
$A_9$ is His, Ala, Gly or D-Pro, or an equivalent amino acid thereof,
$A_{10}$ is Ala, Asn, Gly Lys, Asp or D-Pro, or an equivalent amino acid thereof;
$A_{11}$ is Ala, Gly, Leu or Lys, or an equivalent amino acid thereof;
$A_{12}$ is Ala or Gly, or an equivalent amino acid thereof;
$A_{13}$ is Ala, Gly or Lys, or an equivalent amino acid thereof;
$A_{14}$ is Ala, Gly, His, Ser, Asp, Lys or D-Pro, or an equivalent amino acid thereof;
$A_{15}$ is Ala, Gly, Ile, D-Pro or Leu, or an equivalent amino acid thereof;
$A_{16}$ is Asn, Ala, Gly, D-Pro or Gln, or an equivalent amino acid thereof;
$A_{17}$ is Ala, Asp, Gly, Ser, Lys or D-Pro, or an equivalent amino acid thereof;
$A_{18}$ is Lys, or an equivalent amino acid thereof;
$A_{19}$ is Arg or Glu, or an equivalent amino acid thereof;
$A_{20}$ is Arg, or an equivalent amino acid thereof;
$A_{21}$ is Arg, Lys, Asp or Val, or an equivalent amino acid thereof;
$A_{22}$ is Asp, Lys, Orn or Glu, or an equivalent amino acid thereof;
$A_{23}$ is Leu, Phe or Trp, or an equivalent amino acid thereof;
$A_{24}$ is Leu, or an equivalent amino acid thereof;
$A_{25}$ is Arg, His, Asp, Lys or Glu, or an equivalent amino acid thereof;
$A_{26}$ is Lys or His, or an equivalent amino acid thereof;
$A_{27}$ is Leu or Lys, or an equivalent amino acid thereof;
$A_{28}$ is Ile or Leu, or an equivalent amino acid thereof;
$A_{29}$ is Ala, Asp, Glu or Gln, or an equivalent amino acid thereof;
$A_{30}$ is Asp, Lys or Glu, or an equivalent amino acid thereof;
$A_{31}$ is Ile, Leu or Val, or an equivalent amino acid thereof;
$A_{32}$ is His, or an equivalent amino acid thereof;
$A_{33}$ is Asn or Thr, or an equivalent amino acid thereof; and
$A_{34}$ is Ala or Phe, or an equivalent amino acid thereof; and
$A_{35}$ is absent or a peptide of from 1 to 4 amino acids.

The foregoing peptide compounds are disclosed in WO 98/51324 to possess useful properties, more particularly pharmaceutical properties. They are especially useful for treating disease states capable of being modulated by compounds which bind to parathyroid hormone receptors either with or without comcommitant stimulation of adenylyl cyclase activity. The present invention is directed to an improved method for synthesizing these peptide compounds.

The solid phase synthesis of cyclic peptides typically involves the sequential addition of amino acids to a peptide synthesis resin to obtain a resin-bound peptide possessing all or a portion of the amino acid sequence of the desired cyclic peptide. The amino acid side chain residues to be cyclized are then deprotected and cyclization is effected. If cyclization is effected prior to completion of the entire amino acid sequence, the remaining amino acids are added and the completed peptide is then cleaved from the resin and purified.

However, the linear approach to the preparation of peptides, and to cyclic peptides in general, is frequently inefficient and may therefore not be cost effective for the preparation of large quantities of peptide. In cases where a peptide is assembled in a linear fashion, the ease of purification of the peptide decreases as the number of amino acid residues in the peptide increases. Furthermore, for cyclic peptides, preparing side-chain bridge(s) near the end of the synthesis imparts the problems associated with preparing the side-chain bridge, including low yield, side-reactions and removal of impurities, to the entire peptide. Consequently, the incorporation of a cyclic unit in a lengthy peptide increases the difficulties inherent in linear peptide syntheses. A commercially feasible synthesis of cyclic hPTH analogues such as those disclosed in WO 98/51324 and set forth above requires a synthetic approach which overcomes both the complicating factors of of length and cyclic components and which would enable preparation of commercially useful quantities in the context of drug manufacturing. The present invention is directed to a more efficient preparation of cyclic hPTH and hPTHrP analogues via a process using bridged and non-bridged fragments.

SUMMARY OF THE INVENTION

This invention is directed to a method of preparing cyclic hPTH and hTPHrP analogs of formula

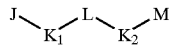

II wherein

J, L, and M are linear peptide fragments $K_1$ is absent or a cyclic peptide fragment, and $K_2$ is a cyclic peptide fragment;

this method comprising the steps of:

(1) preparing

by sequential attachment of suitably protected amino acid residues to a resin to provide:

III where

is a suitable peptide synthesis resin and M is a polypeptide fragment (2) preparing separately by conventional peptide synthesis N-terminal protected cyclic polypeptide fragment of formula IV

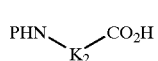

IV wherein P is a suitable amine protecting group, (3) Coupling III with IV to provide a peptide of formula V

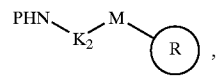

V (4) when cyclic peptide $K_1$ is absent, then (a) polypeptide fragments J and L are prepared as a single polypeptide of formula VI

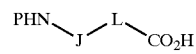

VI and polypeptide VI is coupled to peptide V to provide a peptide of formula VII

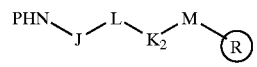

VII or, optionally, (b) the protected individual amino acid elements of polypeptides J and L are added sequentially to the peptide fragment of formula V, or, optionally, (c) either or both J and L are prepared separately as polypeptide fragments and coupled to the growing peptide starting with the fragment of formula V, (5) when cyclic peptide $K_1$ is present, then (a) a polypeptide fragment of formula VIII

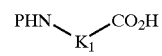

VIII wherein

P is a suitable amine protecting group, is prepared separately by conventional peptide synthesis procedures, (b) a peptide fragment of formula IX

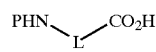

IX is prepared and coupled with peptide fragment V to provide a peptide fragment of formula X

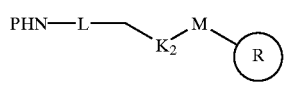

X and (c) the cyclic peptide fragment VIII is coupled with the peptide fragment of formula X to provide a peptide fragment of formula XI

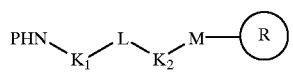

XI (d) peptide fragment of formula XII is prepared

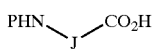
XII and fragment XII is coupled with fragment XI, and (6) cleaving the resin and deprotecting.

In the process described herein, cyclic peptide fragments are prepared separately for coupling with a resin or resin-bound peptide. The separate preparation of the cyclic peptide fragment allows for the convergent synthesis of resin bound cyclic peptides, resulting in increased yield and throughput of the resulting cyclic peptide. Difficulties associated with preparing the bridged fragment are confined to a smaller peptide subunit, which can be purified prior to coupling with the solid phase synthesis resin. The practice of this technique in the context of certain preferred hPTH and hPTHrP analogs requires the synthesis of new peptide fragments and new sequences of events.

DETAILED DESCRIPTION OF THE INVENTION

As used above and throughout the specification, the following terms, unless otherwise indicated, shall be understood to have the following meanings.

Definitions of Terms

"Alkyl" means an aliphatic hydrocarbon group which may be straight or branched having about 1 to about 20 carbon atoms in the chain. Branched means that one or more lower alkyl groups are attached to a linear alkyl chain. "Lower alkyl" means about 1 to 4 carbon atoms in the chain which may be straight or branched. Alkyl groups are exemplified by methyl, ethyl, n- and iso-propyl, n-, sec-, iso- and tert-butyl, and the like.

"Alkenyl" means aliphatic hydrocarbon group containing a carbon-carbon double bond and which may be straight or branched having about 2 to about 20 carbon atoms in the chain. "Lower alkenyl" means about 2 to 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkynyl" means aliphatic hydrocarbon group containing a carbon-carbon triple bond and which may be straight or branched having about 2 to about 20 carbon atoms in the chain. "Lower alkynyl" means about 2 to 4 carbon atoms in the chain which may be straight or branched. Exemplary alkynyl groups include ethynyl, propynyl, n-butynyl, 3-methylbut-2-ynyl, n-pentynyl, heptynyl, octynyl and decynyl.

"Alkylene" means a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

"Phenylalkyl" means a phenyl group attached to the parent molecular moiety through an alkylene group. The alkylene group is preferably of about 1 to about 7 carbon atoms. Representative phenylalkyl groups include benzyl, 2-phenylethyl, 2-propylphenyl, and the like.

"Amine protecting group" means an easily removable group which is known in the art to protect an amino group against undesirable reaction during synthetic procedures and to be selectively removable. The use of N-protecting groups is well known in the art for protecting groups against undesirable reactions during a synthetic procedure and many such protecting groups are known, cf. for example, T. H. Greene and P. G. M. Wuts, Protective Groups in Organic Synthesis, 2nd edition, John Wiley & Sons, New York (1991), incorporated herein by reference. Preferred N-protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC, or Boc), 1,1-dimethylpropynyloxycarbonyl, benzyloxycarbonyl (CBZ), p-nitrophenylsulfinyl, p-nitrobenzyloxycarbony, 2,4-dichlorobenzyloxycarbonyl, allyoxycarbonyl (Alloc), and the like.

"Amino acid" means an amino acid selected from the group consisting of natural and unnatural amino acids as defined herein. The amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are α-amino acids. The most preferred amino acids are α-amino acids having L stereochemistry at the α-carbon.

"Amino acid residue" means the individual amino acid units incorporated into a peptide or peptide fragment.

"Natural amino acid" means an α-amino acid selected from the group consisting of alanine, valine, leucine, isoleucine, proline, phenylalanine, tryptophan, methionine, glycine, serine, threonine, cysteine, tyrosine, asparagine, glutamine, lysine, arginine, histidine, aspartic acid and glutamic acid.

"Unnatural amino acid" means an amino acid for which there is no nucleic acid codon. Examples of unnatural amino acids include, for example, the D-isomers of the natural a-amino acids as indicated above; Aib (aminobutyric acid), bAib (3-aminoisobutyric acid), Nva (norvaline), β-Ala, Aad (2-aminoadipic acid), bAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), aIle (allo-isoleucine), Nle (norleucine), tert-Leu, Cit (citrulline), Orn, Dpm (2,2'-diaminopimelic acid), Dpr (2,3-diaminopropionic acid), α- or β-Nal, Cha (cyclohexyl-Ala), hydroxyproline, Sar (sarcosine), and the like; cyclic amino acids; $N^{\alpha}$-alkylated amino acids such as MeGly ($N^{\alpha}$-methylglycine), EtGly ($N^{\alpha}$-ethylglycine) and EtAsn ($N^{\alpha}$-ethylasparagine); and amino acids in which the α-carbon bears two side-chain substituents.

"Equivalent amino acid" means an amino acid which may be substituted for another amino acid in the peptides according to the invention without any appreciable loss of function. In making such changes, substitutions of like amino acids is made on the basis of relative similarity of side chain substituents, for example regarding size, charge, hydrophilicity, hydropathicity and hydrophobicity as described herein.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

"Peptide" and "polypeptide" mean a polymer in which the monomers are amino acid residues joined together through amide bonds. Preferred peptides of the present invention are those comprising α-amino acids. The most preferred peptides of the present invention comprise α-amino acids having L stereochemistry at the α-carbon.

"Cyclic peptide" means a peptide containing one or more cyclic peptide fragments as defined herein.

"Peptide fragment" means a peptide subunit of the parent peptide. "Peptide fragment" may imply a linear, branched, or cyclic subunit of the target peptide.

"Linear Peptide" means a peptide or polypeptide in which the amino acids are linked to one another via an amid bond between the N-terminal of one and the C-terminal or another.

"Branched peptide" means a peptide or polypeptide within which one or several constituent individual amino acids bearing carboxylic acid or amine side chains are attached to another peptide substituent via these side chains.

"Cyclic peptide fragment" means a peptide fragment as defined herein in which a substituent on one amino acid residue is linked to a substituent on another amino acid residue in the peptide fragment. The linking is preferably between the side chains of two amino acid residues in the peptide fragment, preferably through an ester, amide, disulfide or lanthionine bond. The bonding between the two amino acid side chains is designated herein as

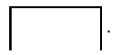.

The ester, amide, disulfide or lanthionine bond which links two amino acid residues of the cyclic peptide is formed between the side-chain functionalities. Thus, an amide is bond is formed between the side-chain carboxyl group of an acidic amino acid residue and the side-chain amino group of a basic amino acid residue; ester bonds are formed between the side-chain carboxyl group of an acidic amino acid residue and the side-chain hydroxyl group of a hydroxyl-containing amino acid residue; disulfides are formed from amino acid residues containing side chain sulfhydryl groups; and lanthionine bridges are formed by desulfurization of the corresponding disulfide.

The number of atoms in the bridge resulting from the amide, ester, disulfide or lanthionine bond formed as described above will vary depending on the length of the side chain and the type of bond (ie, amide, ester, disulfide or lanthionine). The bridge preferably comprises from 2 to 12 atoms, more preferably from 6 to 10 atoms. The most preferred number of atoms contained in the bridge is 7, this bridge preferably comprising an amide bond between the side-chain functionalities of a Lys and an Asp residue.

"Resin" means a solid support modified with a reactive group such that the solid support is amenable to coupling with the carboxy or N-terminus of an amino acid, peptide, or cyclic peptide fragment as defined herein. Representative resins include Merrifield resin (chloromethylated polystyrene), hydroxymethyl resin, 2-chlorotrityl chloride resin, trityl chloride resin, Rink acid resin (4-benzyloxy-2', 4'-dimethoxybenzhydrol resin), trityl alcohol resin, PAM resin (4-hydroxymethyl-phenylacetamidomethyl resin), Wang resin (p-benzyloxybenzyl alcohol resin), MBHA resin (p-methylbenzhydrylamine resin), BHA resin (benzyhydrylamine resin), Rink amide resin (4-(2',4'-dimethoxyphenyl-Fmoc-aminomethyl)phenoxy resin) and PAL resin (5-(4-Fmoc-aminomethyl-3,5-dimethoxyphenoxy)valeric acid-MBHA resin). Preferred resins are chlorotrityl resin, Rink acid resin and Rink amide resin.

"Solid support" means a substrate which is inert to the reagents and reaction conditions described herein, as well as being substantially insoluble in the media used. Representative solid supports include inorganic substrates such as kieselguhr, silica gel, and controlled pore glass; organic polymers including polystyrene, including 1–2% copolystyrene divinyl benzene (gel form) and 20–40% copolystyrene divinyl benzene (macro porous form), polypropylene, polyethylene glycol, polyacrylamide, cellulose, and the like; and composite inorganic/polymeric compositions such as polyacrylamide supported within a matrix of kieselguhr particles. See J. M. Stewart and J. D. Young, *Solid Phase Peptide Synthesis,* 2nd. Ed., Pierce Chemical Co. (Chicago, Ill., 1984).

In addition, "solid support" includes a solid support as described above which is affixed to a second inert support such as the pins described in Technical Manual, Multipin™ SPOC, Chiron Technologies (1995) and references therein which comprise a detachable polyethylene- or polypropylene-based head grafted with an amino functionalized methacrylate copolymer and an inert stem.

In addition, "solid support" includes polymeric supports such as the polyethylene glycol supports described by Janda et al., *Proc. Natl. Acad. Sci. USA,* 92, 6419–6423 (1995) and S. Brenner, WO 95/16918, which are soluble in many solvents but can be precipitated by the addition of a precipitating solvent.

The names of natural and unnatural amino acids and residues thereof used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and residues thereof employed in this specification and appended claims differ from those noted, differing names and abbreviations will be made clear.

A representative peptide prepared according to the process of this invention is denoted, for example, as cyclo (Lys$^{18}$-Asp$^{22}$)[Ala$^1$, Nle$^8$, Lys$^{18}$, Asp$^{22}$,Leu$^{27}$]hPTH(1–31) NH$_2$ with the linked amino acid residues in the parenthesis following "cyclo" and with substituted amino acids from the natural sequence placed in brackets. hPTH stands for human parathyroid hormone, and hPTHrP for human parathyroidhormone-related protein. The numbers in the second parenthesis refer to the number of amino acid residues in the peptide, beginning at the N-terminus (ie, the first 31 amino acids of hPTH).

Preferred Embodiments

As shown in Scheme 1, the preparation of a resin-bound cyclic peptide involves coupling cyclic and noncyclic peptide fragments to a resin, resin bound amino acid, or resin bound peptide.

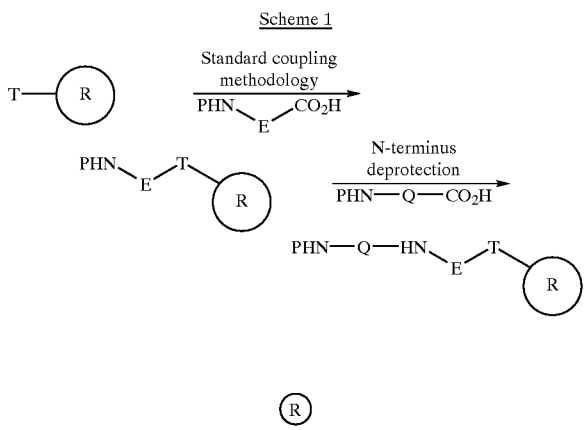

is a resin suitable for peptide synthesis.

T is an H₂N, and amino acid, or a cyclic or acyclic peptide.

E and Q are each or independently an N terminal protected amino acid, or an N-terminal protected cyclic or acyclic peptide fragment.

The coupling is preferably accomplished between the carboxy terminus of the peptide fragment and the resin, resin-bound amino acid or resin bound peptide. When the peptide fragment is coupled to a resin-bound amino acid or peptide, the coupling is preferably through an amide bond between the carboxy terminus of the cyclic peptide fragment and the N-terminus of the resin-bound amino acid or peptide.

In order for the coupling reaction to proceed, the carboxyl group of the peptide fragment must be activated. Many methods of activation may be used in the practice of the invention and include, for example, preformed symmetrical anhydrides (PSA), preformed mixed anhydride (PMA), acid chlorides, active esters, and in situ activation of the carboxylic acid, as set forth in Fields and Noble, 1990, "Solid phase peptide synthesis utilizing 9-fluorenylmethoxycarbonyl amino acids", Int. J. Pept. Protein Res. 35:161–214.

Representative activating agents include isopropyl chloroformate, diisopropylcarbodiimide (DIC), DIC admixed with 1-hydroxybenzotriazole (HOBT), 1-(3-dimethylaminopropyl)-3-ethylcarbodiimide (EDC), bis(2-oxo-3-oxazolidinyl)phosphonic chloride (BOP-Cl), benzotriazole-1-yloxy-tris((dimethylamino)phosphonium) hexafluorophosphate (BOP), benzotriazole-1-yloxy-tris-pyrrolidino-phosphonium hexafluorophosphate (PyBOP), bromo-tris-pyrrolidino-phosphonium hexafluorophosphate (PyBROP), O-(7-azabenzotriazol-1-yl)-N,N,N',N'-tetramethyluronium hexafluorophosphate (HATU), 2-(1H-benzotriazole-1-yl)-1.1.3.3-tetramethyluronium tetrafluoroborate (TBTU), 2-(1H-benzotriazole-1-yl)-1.1.3.3-tetramethyluronium hexafluorophosphate (HBTU), 2-[2-oxo-1-(2H)-pyridyl]-1,1,3,3-bispentamethyleneuronoium tetrafluoroborate (TOPPipU), N,N'-dicyclohexylcarbodiimide (DCC), DCC admixed with HOBT, and the like. Suitable solvents for the coupling reaction include dichloromethane, DMF, DMSO, toluene, THF, and the like. Coupling times range from about 1 to about 48 hours, depending upon the resin and carboxylic acid derivative to be coupled, activating agent, solvent and temperature. The coupling is accomplished at from about −10° C. to about 50° C., preferably at about ambient temperature.

In order to prevent interference with the above-described coupling reaction, the N-terminus of the cyclic peptide fraction is protected by an acid or base sensitive group. Such protecting groups should have the properties of being stable to the conditions of amide bond formation, while being readily removable without destruction of the growing peptide chain or racemization of any of the chiral centers contained therein. Suitable protecting groups are 9-fluorenylmethyloxycarbonyl (FMOC or Fmoc), t-butyloxycarbonyl (BOC or Boc), benzyloxycarbonyl (Cbz), biphenylisopropyloxycarbonyl, t-amyloxycarbonyl, isobornyloxycarbonyl, (α,α)dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is preferred.

Likewise, it may be necessary to protect any reactive side-chain functional groups in the cyclic peptide fragment. Particularly preferred side chain protecting groups are, for side chain amino groups as in lysine and arginine: 2,2,5,7,8-pentamethylchroman-6-sulfonyl (Pmc, PMC or pmc), nitro, p-toluenesulfonyl, 4-methoxybenzenesulfonyl, Cbz, Boc, Alloc (allyloxycarbonyl) and adamantyloxycarbonyl; for tyrosine: benzyl, o-bromobenzyloxycarbonyl, 2,6-dichlorobenzyl, isopropyl, t-butyl (t-Bu), cyclohexyl, cyclopenyl and acetyl (Ac); for serine: t-butyl, benzyl and tetrahydropyranyl; for histidine: trityl, benzyl, Cbz, p-toluenesulfonyl and 2,4-dinitrophenyl; for tryptophan: formyl and Boc; for asparagine and glutamine: Trt (trityl); for aspartic acid and glutamic acid: O-t-Bu and OAllyl and Obenzyl.

Coupling of the fragments to the resin or resin bound peptide is preferably accomplished at about ambient temperature using about 2 molar equivalents (relative to resin) of the Fmoc-protected cyclic peptide fragment, activated with about an equimolar portion of benzotriazolyloxy-tris[pyrrolidino]-phosphonium hexafluoroacetate (PyBOP) and hydroxybenzotriazole hydrate in the presence of about 4 equivalents of diisopropylethyl amine in dimethylformamide over about 16–48 hours.

The completeness of coupling should be assessed. Those skilled in the art would be familiar with the well known monitoring tests such as ninhydrin (the Kaiser test), picric acid, 2,4,6-trinitro-benzenesulfonic (TNBS), fluorescamine, and chloranil, which are based on reagent reaction with free amino groups to produce a chromophoric compound. If imino acids (e.g., Pro and Hyp) are used, isatin monitoring is a preferred method. Fields and Noble, supra. Quantification of reaction completeness may be monitored during the course of the reaction, e.g., as described by Salisbury et al. (International Patent Publication No. WO91/03485).

With Fmoc synthesis, the Kaiser and TNBS tests are preferred. In the Kaiser test, a sample of resin peptide can be tested with ninhydrin reagent obtained from Pierce Chemical in the method set forth by Sarin et al. (1981, Anal. Biochem. 117:147–157.). Similarly, a sample of resin peptide L can be tested using trinitrobenzenesulfonic acid (TNBS), available from Fluka, as set forth by Takajashi (1984, Chem Lett. 1: 127)

If the coupling reaction is incomplete as determined by one or the other of these tests, the reaction can be forced to completion by several methods familiar to those in the art, including (a) a repeat coupling using a one to five fold excess of protected amino acid, (b) a repeat coupling using different or additional solvents (e.g., trifluoroethane), or (c) the addition of chaotropic salts, e.g., NaClO$_4$ or LiBr (Klis and Stewart, 1990, "Peptides: Chemistry, Structure and Biology," Rivier and Marshall, eds., ESCOM Publ., p. 904–906).

A preferred resin-bound cyclic peptide fragment has formula II

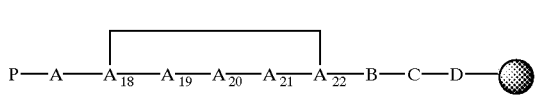

II wherein

is a resin;

P is an amine protecting group;

A is absent or a group of formula

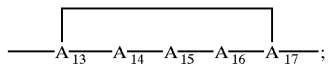

B is a group of formula —$A_{23}$—$A_{24}$—$A_{25}$—;

C is a group of formula —$A_{26}$—$A_{27}$—$A_{28}$—$A_{29}$—$A_{30}$—;

and

D is —$A_{31}$—, —$A_{31}$—$A_{32}$—, —$A_{31}$—$A_{32}$—$A_{33}$— or —$A_{31}$—$A_{32}$—$A_{33}$—$A_{34}$—;

wherein

is a lactam, ester, disulfide or lanthionine bridge; $A_{13}$, $A_{17}$, $A_{18}$ and $A_{22}$ are amino acid residues; $A_{14}$ is His(Trt) or Ser(tBu); $A_{15}$ and $A_{28}$ are independently Ile or Leu; Ser(tBu) or Leu; $A_{16}$ is Asn(Trt) or Gln(Trt); $A_{19}$ is Arg(Pmc) or Glu(OtBu); $A_{20}$ is Arg(Pmc); $A_{21}$ is Arg(Pmc) or Val; $A_{23}$ is Phe or Trp(Boc); $A_{24}$ is Leu; $A_{25}$ is Arg(Pmc) or His(Trt); $A_{26}$ and $A_{30}$ are amino acid residues wherein the side chains of $A_{26}$ and $A_{30}$ are optionally linked through an amide, disulfide or lanthionine bond; $A_{27}$ is Leu or Lys(Boc); $A_{29}$ is Ala or Gln(Trt); $A_{31}$ is Ile or Val; $A_{32}$ is His(Trt); $A_{33}$ is Asn(Trt) or Thr(tBu); and $A_{34}$ is Ala or Phe.

Another preferred resin-bound cyclic peptide fragment has formula II wherein

is a lactam bridge and the side chains of $A_{26}$ and $A_{30}$ are optionally linked through an amide bond.

Another preferred resin-bound cyclic peptide has formula II wherein

is a lactam bridge; $A_{13}$ and $A_{18}$ are Lys; $A_{17}$ and $A_{22}$ are Asp; and $A_{26}$ is Lys(Boc); and $A_{30}$ is Asp(OtBu); or the side chains of $A_{26}$ and $A_{30}$ are optionally linked through an amide bond.

Another preferred resin-bound cyclic peptide fragment has formula III

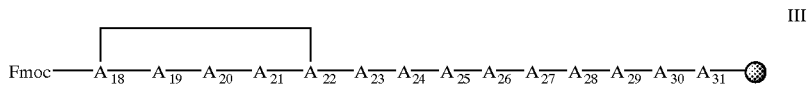

III wherein

is a lactam bridge;

$A_{18}$ is Lys; $A_{19}$ is Glu(OtBu); $A_{20}$ is Arg(Pmc); $A_{21}$ is Val; $A_{22}$ is Asp, $A_{23}$ is Trp(Boc); $A_{24}$ is Leu; $A_{25}$ is Arg(Pmc); $A_{26}$ is Lys(Boc); $A_{27}$ is Leu; $A_{28}$ is Leu; $A_{29}$ is Gln(Trt); $A_{30}$ is Asp(OtBu); and $A_{31}$ is Val.

The resin-bound peptide prepared as described above may be further elaborated, for example by coupling with one or more additional cyclic peptide fragments, by coupling with one or more peptide fragments, by sequential addition of individual amino acids, or by any combination of the foregoing.

The complete cyclic peptide is then cleaved from the resin and purified. Protecting groups may be removed prior or subsequent to, or simultaneously with, cleavage from the resin. The fully deprotected peptide may purified, alone or in combination, by acid-base extraction, recrystallization, lyophilization, by a sequence of chromatographic steps employing any or all of the following types: ion exchange on a weakly basic resin in the acetate form; hydrophobic adsorption chromatography on underivitized polystyrene-divinylbenzene (for example, AMBERLITE® XAD); silica gel adsorption chromatography; ion exchange chromatography on carboxymethylcellulose; partition chromatography, e.g. on SEPHADEX® G-25, LH-20 or countercurrent distribution; high performance liquid chromatography (HPLC), especially reverse-phase HPLC on octyl- or octadecylsilyl-silica bonded phase column packing.

Preparation of the Peptide Fragment

The fragment is prepared by synthesizing the peptide backbone, which entails assembling the amino acids comprising the fragment in their proper order. The peptide backbone of the fragment may be synthesized by any of the techniques that are known to those skilled in the art. For solid phase peptide synthesis, a summary of the many techniques may be found in J. M. Stewart and J. D. Young, *Solid Phase Peptide Synthesis*, W.H. Freeman Co. (San Francisco), 1963 and J. Meienhofer, *Hormonal Proteins and Peptides*, vol. 2, p. 46, Academic Press (New York), 1973. For classical solution synthesis see G. Schroder and K. Lupke, *The Peptides*, vol. 1, Acacemic Press (New York), 1965.

As would be known to those of ordinary skill in the art, the process of peptide synthesis on solid supports generally involves building a peptide from the carboxyl or C-terminal end in which the C-terminal amino acid with its ax-amino group protected is attached to a solid phase polymer. The N-protecting group is then cleaved off, and the next amino acid, also N-protected, is coupled by a peptide bond to the α-amino group of the amino acid attached to the solid support as described above. The cycle of deprotection of the prior amino acid and coupling the additional amino acid is repeated until the peptide is completed. Any reactive side chains of the amino acids are protected by chemical groups that can withstand the coupling and $N^\alpha$-deprotection procedure but can be removed at the end of the synthesis. When the peptide fragment is prepared using solid phase methods, the fragment is obtained for use in couplings to other fragments by cleavage from the resin.

A cyclic fragment is prepared in similar fashion. However, backbone assembly is followed by (1)selective deprotection of the side-chain functionalities to be cyclized, (2)cyclization, and (3)optional removal of any remaining protecting groups.

The use of Fmoc amino acids is but one strategy of peptide synthesis. A Boc (t-butyloxycarbonyl-protected amino group) strategy may also be used to prepare a peptide bound to the solid support (e.g., Geysen et al., 1987, J. Immunol. Methods 102:259–274.)

Amino acids used for peptide synthesis may be standard Boc ($N^\alpha$-amino protected $N^\alpha$-t-butyloxycarbonyl) amino acids described by Merrifield (1963, J. Am. Chem. Soc. 85:2149–2154), or the base-labile $N^\square$-amino protected 9-fluorenylmethoxycarbonyl (Fmoc) amino acids first described by Carpino and Han (1972, J. Org. Chem. 37:3403–3409). Both Fmoc and Boc $N^\square$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\square$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS.

Although C-terminal to N-terminal peptide synthesis is the standard, those of ordinary skill in the art will recognize that the peptide fragment is also amenable to synthesis from N-terminus to C-terminus.

Preparation of the Lactam-Bridge

Lactam-bridged cyclic peptide fragments are prepared by formation of an amide bond between the side-chain carboxyl group of an acidic amino acid residue and the side-chain amino group of a basic amino acid residue in the presence of an activating agent as described above. Preferred acidic amino acid residues include Asp, Glu, —NHCH[$(CH_2)_3$ $CO_2H$]CO— and —NHCH[$(CH_2)_4CO_2H$]CO—, Asp being most preferred. Preferred basic amino acid residues include His, Lys, Orn, —NHCH($CH_2NH_2$)CO— and —NHCH [$(CH_2)_2NH_2$]CO—, Lys being most preferred.

In instances wherein the peptide precursor to the cyclic peptide fragment contains more than one acidic or basic amino acid residue, protecting groups for the additional acidic or basic amino acids in the cyclic peptide fragment are selected so that the amino acids to be cyclized may be selectively deprotected. Preferably, the desired acidic and basic amino acid residues are deprotected simultaneously. Furthermore, in addition to being stable to the reagents used to deprotect the selected basic and acidic amino acid residues, the protecting groups on the remaining amino acid residues are selected to be stable to the cyclization conditions employed.

The term "orthogonality" when used in reference to side chain protecting groups refers to a situation as described herein in which there are two or more classes of protecting groups on a molecule, each class most optimally removed under specific conditions, while remaining stable to conditions used to remove protecting groups in other classes. Thus one can remove all protecting groups of one class, while leaving all others intact.

Preferred protecting groups having the desired orthogonality are: for the acidic amino acid residue to be cyclized: allyl; for the basic amino acid residue to by cyclized: allyloxycarbonyl (alloc); for any additional acidic amino acid residues: tert-butyl (tBu); and for any additional basic amino acid residues: tert-butyloxycarbonyl (Boc).

Following synthesis of the peptide backbone of the cyclic peptide fragment using solid phase or solution phase techniques, the allyl and allyloxycarbonyl protecting groups are removed simultaneously by treatment with palladium, preferably tetrakis(triphenylphosphine) palladium(0) in the presence of N-methylaniline. Formation of the lactam bridge is then accomplished as described herein for amide bond formation.

Preferred cyclic peptide fragments for use in preparing the resin-bound cyclic peptides of this invention have formula XV, XVI or XVII

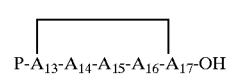

XV

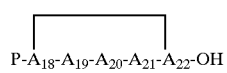

XVI

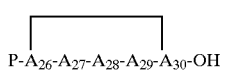

XVII wherein

is a lactam, disulfide or lanthionine bridge;

P is an amine protecting group;

$A_{13}$, $A_{17}$, $A_{18}$, $A_{22}$, $A_{26}$ and $A_{30}$ are amino acid residues; $A_{14}$ is His(Trt) or Ser(tBu); $A_{15}$ is Ser(tBu) or Leu; $A_{16}$ is Asn(Trt) or Gln(Trt); $A_{19}$ is Arg(Pmc) or Glu(OtBu); $A_{20}$ is Arg(Pmc); $A_{21}$ is Arg(Pmc) or Val; $A_{27}$ is Leu or Lys(Boc); $A_{28}$ is Ile or Leu; and $A_{29}$ is Ala or Gln(Trt).

More preferred cyclic peptide fragments have formula IV, V or VI wherein

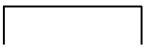

is a lactam bridge;

P is Fmoc;

$A_{13}$, $A_{18}$ and $A_{26}$ are Lys; $A_{17}$, $A_{22}$ and $A_{30}$ are Asp; $A_{14}$ is His(Trt) or Ser(tBu); $A_{15}$ is Ser(tBu) or Leu; $A_{16}$ is Asn(Trt) or Gln(Trt); $A_{19}$ is Arg(Pmc) or Glu(OtBu); $A_{20}$ is Arg(Pmc); $A_{21}$ is Arg(Pmc) or Val; $A_{27}$ is Leu or Lys(Boc); $A_{28}$ is Ile or Leu; and $A_{29}$ is Ala or Gln(Trt).

A still more preferred cyclic peptide fragment for use in preparing the resin-bound cyclic peptides of this invention is Fmoc-cyclo(Lys-Asp)Lys-Glu(OtBu)-Arg(Pmc)-Val-Asp-OH.

Cyclic peptide parathyroid hormone analogs and parathyroid hormone-related protein analogs suitable for preparation using the process of this invention are disclosed by:

1. Condon et al., U.S. Ser. No. 60/046,472 (filed May 14, 1997);
2. Willick et al., U.S. Pat. No. : 5,556,940 (Sep. 17, 1997);
3. Chorev et al., U.S. Pat. No. 5,717,062 (Feb. 10, 1998);
4. Vickery et al., WO 96/40775 (published Dec. 19, 1996).

A preferred cyclic peptide suitable for preparation using the process of this invention has formula I $A_{18}$ and $A_{22}$ are amino acid residues wherein the side chains of $A_{18}$ and $A_{22}$ are linked by an amide bond;

$A_{19}$ is Arg or Glu or an equivalent amino acid residue thereof;

$A_{20}$ is Arg or an equivalent amino acid residue thereof;

$A_{21}$ is Arg or Val or an equivalent amino acid residue thereof;

$A_{23}$ is Phe or Trp or an equivalent amino acid residue thereof;

$A_{24}$ is Leu or an equivalent amino acid residue thereof;

$A_{25}$ is Arg or His or an equivalent amino acid residue thereof;

$A_{26}$ and $A_{30}$ are amino acid residues wherein the side chains of $A_{26}$ and $A_{30}$ are optionally linked through an amide bond;

$A_{27}$ is Leu or Lys or an equivalent amino acid residue thereof;

$A_{29}$ is Ala or Gln or an equivalent amino acid residue thereof;

$A_{31}$ is Ile or Val or an equivalent amino acid residue thereof;

Y is selected from the group consisting of (a) $R_3$, (b) $A_{32}$—$R_3$, (c) —$A_{32}$—$A_{33}$—$R_3$ and (d)—$A_{32}$—$A_{33}$—$A_{34}$—$R_3$ wherein $R_3$ is —OH or —$NR_4R_5$ wherein $R_4$ and $R_5$ are independently from hydrogen and lower alkyl, $A_{32}$ is His or an equivalent amino acid residue thereof, $A_{33}$ is Asn or Thr or an equivalent amino acid residue thereof and $A_{34}$ is Ala or Phe or an equivalent amino acid residue thereof.

Peptides of formula I possess useful pharmaceutical properties. They are especially useful for treating disease states

I wherein

X is selected from the group consisting of (a) $R_{1a}$—$A_1$—$A_2$—$A_3$—$A_4$—$A_5$—$A_6$— (b) $R_{1b}$—$A_2$—$A_3$—$A_4$—$A_5$—$A_6$—, (c) $R_{1b}$—$A_3$—$A_4$—$A_5$—$A_6$—, (d) $R_{1b}$—$A_4$—$A_5$—$A_6$—, (e)$R_{1b}$—$A_5$—$A_6$—, (f) $R_{1b}$—$A_6$— and (g) $R_{1b}$— wherein $R_{1a}$ is selected from the group consting of (1) H, (2) a peptide comprising from 1 to 6 amino acids, (3) alkyl, (4) phenylalkyl, (5) —$COR_2$ wherein $R_2$ is selected from alkyl, alkenyl, alkynyl, phenyl, naphthyl and phenylalkyl, $R_{1b}$ is selected from the group consting of (1) H, (2) alkyl, (3) phenylalkyl and (4) —$COR_2$ wherein $R_2$ is selected from alkyl, alkenyl, alkynyl, phenyl, naphthyl and phenylalkyl, $A_1$ is selected from Ser and Ala or an equivalent amino acid residue thereof, $A_2$, $A_3$, $A_4$ and $A_6$ are amino acid residues and $A_5$ is selected from Ile and His or an equivalent amino acid residue thereof;

$A_7$, $A_9$, $A_{11}$ and $A_{12}$ are amino acid residues;

$A_8$ is Leu or Nle or an equivalent amino acid residue thereof;

$A_{10}$ is Asp or Asn or an equivalent amino acid residue thereof;

$A_{13}$ and $A_{17}$ are amino acid residues wherein the side chains of $A_{13}$ and $A_{17}$ are linked through an amide bond;

$A_{14}$ is His or Ser or an equivalent amino acid residue thereof;

$A_{15}$ and $A_{28}$ are independently Ile or Leu or an equivalent amino acid residue thereof.

$A_{16}$ is Asn or Gln or an equivalent amino acid residue thereof;

capable of being modulated by compounds which bind to parathyroid hormone receptors either with or without concomitant stimulation of cAMPase activity. See U.S. Ser. No. 60/046,472.

Representative preferred cyclic peptides suitable for preparation using the process of this invention include, but are not limited to cyclo(Lys$^{18}$-Asp$^{22}$)[Ala$^1$,Nle$^8$,Lys$^{18}$,Asp$^{22}$,Leu$^{27}$]hPTH (1–31)NH$_2$ (SEQ ID NO: 1);

cyclo(Lys$^{18}$-Asp$^{22}$)[Ala$^{1,2}$,Nle$^8$,Lys$^{18}$,Asp$^{22}$,Leu$^{27}$]hPTH (1–31)NH$_2$ (SEQ ID NO: 2);

cyclo(Lys$^{18}$-Asp$^{22}$)[Ala$^{1,3}$,Nle$^8$,Lys$^{18}$,Asp$^{22}$,Leu$^{27}$]hPTH (1–31)NH$_2$ (SEQ ID NO: 3);

cyclo(Lys$^{18}$-Asp$^{22}$)[Ala$^{1,4}$,Nle$^8$,Lys$^{18}$,Asp$^{22}$,Leu$^{27}$]hPTH (1–31)NH$_2$ (SEQ ID NO: 4);

cyclo(Lys$^{18}$-Asp$^{22}$)[Ala$^{1,5}$,Nle$^8$,Lys$^{18}$,Asp$^{22}$,Leu$^{27}$]hPTH (1–31)NH$_2$ (SEQ ID NO: 5);

cyclo(Lys$^{18}$-Asp$^{22}$)[Ala$^{1,6}$,Nle$^8$,Lys$^{18}$,Asp$^{22}$,Leu$^{27}$]hPTH (1–31)NH$_2$ (SEQ ID NO: 6);

cyclo(Lys$^{18}$-Asp$^{22}$)[Ala$^{1,7}$,Nle$^8$,Lys$^{18}$,Asp$^{22}$,Leu$^{27}$]hPTH (1–31)NH$_2$ (SEQ ID NO: 7);

cyclo(Lys$^{18}$-Asp$^{22}$)[Ala$^{1,8}$,Lys$^{18}$,Asp$^{22}$,Leu$^{27}$]hPTH(1–31) NH$_2$ (SEQ ID NO: 8);

cyclo(Lys$^{18}$-Asp$^{22}$)[Ala$^{1,10}$,Nle$^8$,Lys$^{18}$,Asp$^{22}$,Leu$^{27}$]hPTH (1–31)NH$_2$ (SEQ ID NO: 9);

cyclo(Lys$^{18}$-Asp$^{22}$)[Ala$^{1,11}$,Nle$^8$,Lys$^{18}$,Asp$^{22}$,Leu$^{27}$]hPTH (1–31)NH$_2$ (SEQ ID NO: 10);

cyclo(Lys$^{18}$-Asp$^{22}$)[Ala$^{1,12}$,Nle$^8$,Lys$^{18}$,Asp$^{22}$,Leu$^{27}$]hPTH (1–31)NH$_2$ (SEQ ID NO: 11);

cyclo(Lys$^{18}$-Asp$^{22}$)[Ala$^{1,13}$,Nle$^8$,Lys$^{18}$,Asp$^{22}$,Leu$^{27}$]hPTH (1–31)NH$_2$ (SEQ ID NO: 12);

cyclo(Lys$^{18}$-Asp$^{22}$)[Ala$^{1,14}$,Nle$^8$,Lys$^{18}$,Asp$^{22}$,Leu$^{27}$]hPTH (1–31)NH$_2$ (SEQ ID NO: 13);
cyclo(Lys$^{18}$-Asp$^{22}$)[Ala$^{1,15}$,Nle$^8$,Lys$^{18}$,Asp$^{22}$,Leu$^{27}$]hPTH (1–31)NH$_2$ (SEQ ID NO: 14);
cyclo(Lys$^{18}$-Asp$^{22}$)[Ala$^{1,16}$,Nle$^8$,Lys$^{18}$,Asp$^{22}$,Leu$^{27}$]hPTH (1–31)NH$_2$ (SEQ ID NO: 15);
bicyclo(Lys$^{13}$-Asp$^{17}$,Lys$^{18}$-Asp$^{22}$)[Ala$^1$,Nle$^8$,Lys$^{18}$, Asp$^{17,22}$,Leu$^{27}$]hPTH(1–31)NH$_2$ (SEQ ID NO: 16);
bicyclo(Lys$^{18}$-Asp$^{22}$,Lys$^{26}$-Asp$^{30}$)[Ala$^1$,Nle$^8$,Lys$^{18}$,Asp$^{22}$, Leu$^{27}$]hPTH(1–31)NH$_2$ (SEQ ID NO: 17);
cyclo(Lys$^{18}$-Asp$^{22}$)[Ala$^1$,Nle$^8$,Lys$^{18}$Asp$^{22}$,Leu$^{27}$]hPTH (1–34)NH$_2$ (SEQ ID NO: 18);
bicyclo(Lys$^{13}$-Asp$^{17}$,Lys$^{18}$-Asp$^{22}$)[Ala$^1$,Nle$^8$,Lys$^{18}$, Asp$^{17,22}$, Leu$^{27}$]hPTH(1–34)NH$_2$ (SEQ ID NO: 19);
bicyclo(Lys$^{18}$-Asp$^{22}$Lys$^{26}$-Asp$^{30}$)[Ala$^1$,Nle$^8$,Lys$^{18}$,Asp$^{22}$, Leu$^{27}$]hPTH(1–34)NH$_2$(SEQ ID NO: 46);
cyclo(Lys$^{18}$-Asp$^{22}$)[Lys$^{18}$,Asp$^{22}$]hPTHrP(1–34)NH$_2$ (SEQ ID NO: 20);
cyclo(Lys$^{18}$-Asp$^{22}$)[Lys$^{18,26,30}$,Asp$^{22}$,Leu$^{23,28,31}$,Glu$^{25,29}$] hPTHrP(1–34)NH$_2$ (SEQ ID NO: 21);
cyclo(Lys$^{18}$-Asp$^{22}$)[Nle$^8$,Lys$^{18}$,Asp$^{22}$,Leu$^{27}$]hPTH(7–34) NH$_2$ (SEQ ID NO: 22);
cyclo(Lys$^{18}$-Asp$^{22}$)[Lys$^{18}$,Asp$^{22}$]hPTHrP(7–34)NH$_2$ (SEQ ID NO: 23);
bicyclo(Lys$^{13}$,Asp$^{17}$,Lys$^{18}$,Asp$^{22}$)[Nle$^8$,Lys$^{18}$,Asp$^{22}$,Leu$^{27}$] hPTH(7–34)NH$_2$, and SEQ ID NO: 24); and
bicyclo(Lys$^{18}$-Asp$^{22}$,Lys$^{26}$,Asp30)[Nle$^8$,Lys$^{18}$,Asp$^{22}$, Leu$^{27}$]hPTH(7–34)NH$_2$ (SEQ ID NO: 25).

Another preferred cyclic peptide suitable for preparation using the process of this invention has formula I wherein the amino acid residues are α-amino acid residues having L stereochemistry at the α-carbon.

Another preferred cyclic peptide suitable for preparation using the process of this invention has formula I wherein X is selected from the group consisting of (a) $R_{1a}$—$A_1$—$A_2$—$A_3$—$A_4$—$A_5$—$A_6$— wherein $R_{1a}$ is H or Pro, $A_1$ is Ser or Ala, $A_2$ is Val, $A_3$ is Ser. $A_4$ Glu, $A_5$ is Ile or His, $A_6$ is Gln, (b) $R_{1b}$—,$A_2$—$A_3$—$A_4$—$A_5$—$A_6$— wherein $A_2$,$A_3$,$A_4$,$A_5$ and $A_6$ are defined above and $R_{1b}$ is H, (c) $R_{1b}$—$A_3$—$A_4$—$A_5$—$A_6$— wherein $R_{1b}$, $A_3$, $A_4$, $A_5$ and $A_6$ are defined above, (d) $R_{1b}$—$A_4$—$A_5$—$A_6$— wherein $R_{1b}$,$A_4$,$A_5$ and $A_6$ are defined above, (e) $R_{1b}$—$A_5$—$A_6$— wherein $R_{1b}$,$A_5$ and $A_6$ are defined above, (f) $R_{1b}A_6$— wherein $R_{1b}$ and $A_6$ are defined above and (g) $R_{1b}$— wherein $R_{1b}$ is defined above; $A_7$ is Leu; $A_8$ is Leu or Nle; $A_9$ is His; $A_{10}$ is Asp or Asn; $A_{11}$ is Leu; $A_{12}$ is Gly; $A_{13}$, $A_{17}$, $A_{18}$, $A_{22}$ and $A_{30}$ are independently selected from Ser, Thr, Lys, Cys, homo-Cys Orn, Asp, Glu, —NHCH(CH$_2$NH$_2$)CO—, —NHCH[(CH$_2$)$_2$NH$_2$]CO—, —NHCH[(CH$_2$)$_3$CO$_2$H]CO— and —NHCH[(CH$_2$)$_4$CO$_2$H]CO—; $A_{14}$ is His or Ser; $A_{15}$ is Ser or Leu; $A_{16}$ is Asn or Gln; $A_{19}$ is Arg or Glu; $A_{20}$ is Arg; $A_{21}$ is Arg or Val; $A_{23}$ is Phe or Trp; $A_{24}$ is Leu; $A_{25}$ is Arg or His; $A_{26}$ is His or is independently selected from the group consisting of Ser, Thr, Lys, Cys, homo-Cys, Orn, Asp, Glu, —NHCH(CH$_2$NH$_2$)CO—, —NHCH[(CH$_2$)$_2$NH$_2$]CO—, —NHCH[(CH$_2$)$_3$CO$_2$H]CO— and —NHCH[(CH$_2$)$_4$CO$_2$H]CO—; $A_{27}$ is Leu or Lys; $A_{28}$ is Ile or Leu; $A_{29}$ is Ala or Gln; $A_{31}$ is Ile or Val; and Y is selected from the group consisting of (a) —$R_3$ wherein —$R_3$ is —OH or —NR$_4$R$_5$ wherein R$_4$ and R$_5$ are independently selected from hydrogen and alkyl of one to four carbon atoms, (b) —$A_{32}$—$R_3$ wherein $R_3$ is defined above and $A_{32}$ is His, (c) —$A_{32}$—$A_{33}$—$R_3$ wherein $R_3$ and $A_{32}$ are defined above and $A_{33}$ is Asn or Thr and (d) —$A_{32}$—$A_{33}$—$A_{34}$ wherein $A_{34}$ is Ala or Phe.

Another preferred cyclic peptide suitable for preparation using the process of this invention has formula I wherein
(i) the side chains of $A_{18}$ and $A_{22}$ are linked through an amide bond,
(ii) the side chains of $A_{13}$ and $A_{17}$ are linked through an amide bond, and the side chains of $A_{18}$ and $A_{22}$ are linked through an amide bond,
(iii) the side chains of $A_{18}$ and $A_{22}$ are linked through an amide bond, and the side chains of $A_{26}$ and $A_{30}$ are linked through an amide bond or
(iv) the side chains of $A_{13}$ and $A_{17}$ are linked through an amide bond, the side chains of $A_{18}$ and $A_{22}$ are linked through an amide bond and the side chains of $A_{26}$ and $A_{30}$ are linked through an amide bond.

Another preferred cyclic peptide suitable for preparation using the process of this invention has formula I wherein $A_{13}$ is selected from Lys and Ala, $A_{17}$ is selected from Ser and Asp, $A_{18}$ is Lys, $A_{22}$ is Asp, $A_{26}$ is Lys and $A_{30}$ is Asp.

Another preferred cyclic peptide suitable for preparation using the process of this invention has formula I wherein X is $R_{1a}$—$A_1$—$A_2$—$A_3$—$A_4$—$A_5$—$A_6$—.

Another preferred cyclic peptide suitable for preparation using the process of this invention has formula I wherein $A_1$ is Ala, $A_8$ is Nle and $A_{27}$ is Leu.

Another preferred cyclic peptide suitable for preparation using the process of this invention has formula I wherein $R_{1a}$ is H and Y is NH$_2$.

Another preferred cyclic peptide suitable for preparation using the process of this invention has formula I wherein $R_{1a}$ is H and Y is —$A_{32}$—$A_{33}$—$A_{34}$—NH$_2$.

Another preferred cyclic peptide suitable for preparation using the process of this invention has formula I wherein X is selected from the group consisting of (a) $R_{1b}$—$A_2$—$A_3$—$A_4$—$A_5$—$A_6$—, (b) $R_{1b}$—$A_3$—$A_4$—$A_5$—$A_6$—, (c) $R_{1b}$—$A_4$—$A_5$—$A_6$—, (e) $R_{1b}$—$A_6$— and (f) $R_{1b}$—.

Another preferred cyclic peptide suitable for preparation using the process of this invention has formula I wherein $A_8$ is Nle and $A_{27}$ is Leu.

Another preferred cyclic peptide suitable for preparation using the process of this invention has formula I wherein X is H and Y is —$A_{32}$—$A_{33}$—$A_{34}$—NH$_2$.

More preferred cyclic peptides suitable for preparation using the process of this invention are selected from cyclo (Lys$^{18}$-Asp$^{22}$)[Ala$^1$,Nle$^8$,Lys$^{18}$,Asp$^{22}$,Leu$^{27}$]hPTH(1–31) NH$_2$ (SEQ ID NO: 1);
cyclo(Lys$^{18}$-Asp$^{22}$)[Ala$^{1,2}$,Nle$^8$,Lys$^{18}$,Asp$^{22}$,Leu$^{27}$]hPTH (1–31)NH$_2$ (SEQ ID NO: 2);
cyclo(Lys$^{18}$-Asp$^{22}$)[Ala$^{1,3}$,Nle$^8$,Lys$^{18}$,Asp$^{22}$,Leu$^{27}$]hPTH (1–31)NH$_2$ (SEQ ID NO: 3);
cyclo(Lys$^{18}$-Asp$^{22}$)[Ala$^{1,4}$,Nle$^8$,Lys$^{18}$,Asp$^{22}$,Leu$^{27}$]hPTH (1–31)NH$_2$ (SEQ ID NO: 4);
cyclo(Lys$^{18}$-Asp$^{22}$)[Ala$^{1,5}$,Nle$^8$,Lys$^{18}$,Asp$^{22}$,Leu$^{27}$]hPTH (1–31)NH$_2$ (SEQ ID NO: 5);
cyclo(Lys$^{18}$-Asp$^{22}$)[Ala$^{1,6}$,Nle$^8$,Lys$^{18}$,Asp$^{22}$,Leu$^{27}$]hPTH (1–31)NH$_2$ (SEQ ID NO: 6);
cyclo(Lys$^{18}$-Asp$^{22}$)[Ala$^{1,7}$,Nle$^8$,Lys$^{18}$,Asp$^{22}$,Leu$^{27}$]hPTH (1–31)NH$_2$ (SEQ ID NO: 7);
cyclo(Lys$^{18}$-Asp$^{22}$)[Ala$^{1,8}$,Lys$^{18}$,Asp$^{22}$,Leu27]hPTH(1–31) NH$_2$ (SEQ ID NO: 8);
cyclo(Lys$^{18}$-Asp$^{22}$)[Ala$^{1,10}$,Nle$^8$,Lys$^{18}$,Asp$^{22}$,Leu$^{27}$]hPTH (1–31)NH$_2$ (SEQ ID NO: 9);
cyclo(Lys$^{18}$-Asp$^{22}$)[Ala$^{1,11}$,Nle$^8$,Lys$^{18}$,Asp$^{22}$,Leu$^{27}$]hPTH (1–31)NH$_2$ (SEQ ID NO: 10);
cyclo(Lys$^{18}$-Asp$^{22}$)[Ala$^{1,12}$,Nle$^8$,Lys$^{18}$,Asp$^{22}$,Leu$^{27}$]hPTH (1–31)NH$_2$ (SEQ ID NO: 11);
cyclo(Lys$^{18}$-Asp$^{22}$)[Ala$^{1,13}$,Nle$^8$,Lys$^{18}$,Asp$^{22}$,Leu$^{27}$]hPTH (1–31)NH$_2$ (SEQ ID NO: 12);
cyclo(Lys$^{18}$-Asp$^{22}$)[Ala$^{1,14}$,Nle$^8$,Lys$^{18}$,Asp$^{22}$,Leu$^{27}$]hPTH (1–31)NH$_2$ (SEQ ID NO: 13);
cyclo(Lys$^{18}$-Asp$^{22}$)[Ala$^{1,15}$,Nle$^8$,Lys$^{18}$,Asp$^{22}$,Leu$^{27}$]hPTH (1–31)NH$_2$ (SEQ ID NO: 14);

cyclo(Lys¹⁸-Asp²²)[Ala¹,¹⁶,Nle⁸,Lys¹⁸,Asp²²,Leu²⁷]hPTH
(1–31)NH₂ (SEQ ID NO: 15);
bicyclo(Lys¹³-Asp¹⁷,Lys¹⁸-Asp²²)[Ala¹,Nle⁸,Lys¹⁸,
Asp¹⁷,²²,Leu²⁷]hPTH(1–31)NH₂ (SEQ ID NO: 16); and
bicyclo(Lys¹⁸-Asp²²,Lys²⁶,Asp³⁰)[Ala¹,Nle⁸,Lys¹⁸,Asp²²,
Leu²⁷]hPTH(1–31)NH₂ (SEQ ID NO: 17);

Still more preferred cyclic peptides suitable for preparation using the process of this invention are selected from
cyclo(Lys¹⁸-Asp²²)[Ala¹,Nle⁸,Lys¹⁸,Asp²²,Leu²⁷]hPTH
(1–31)NH₂ (SEQ ID NO: 1);
bicyclo(Lys¹³-Asp¹⁷,Lys¹⁸-Asp²²)[Ala¹,Nle⁸,Lys¹⁸,
Asp¹⁷,²²,Leu²⁷]hPTH(1–31)NH₂ (SEQ ID NO: 16); and
bicyclo(Lys¹⁸-Asp²²,Lys²⁶-Asp³⁰)[Ala¹,Nle⁸,Lys¹⁸,Asp²²,
Leu²⁷]hPTH(1–31)NH₂ (SEQ ID NO: 17);

A still yet more preferred cyclic peptide suitable for preparation using the process of this invention is
cyclo(Lys¹⁸-Asp²²)[Ala¹,Nle⁸,Lys¹⁸,Asp²²,Leu²⁷]hPTH
(1–31)NH₂ (SEQ ID NO: 1);

The foregoing may be better understood by reference to the following example, which is presented for illustration and is not intended to limit the scope of this invention.

EXAMPLE 1

Preparation of cyclo(Lys¹⁸-Asp²²)[Ala¹, Nle⁸,Lys¹⁸,Asp²²,
Leu²⁷]hPTH(1–31)NH₂ (SEQ ID NO: 1)

Ala-Val-Ser-Glu-Ile-Gln-Leu-Nle-His-Asn-Leu-Gly-Lys-His-Leu-Asn-

Ser-Lys-Glu-Arg-Val-Asp-Trp-Leu-Arg-Lys-Leu-Leu-Gln-Asp-Val—NH₂

Step 1
Fmoc-Trp(Boc)-Leu-Arg(Pmc)-Lys(Boc)-Leu-Leu-Gln
(Trt)-Asp(OtBu)-Val-NH-resin (SEQ ID NO: 28)

Rink Amide MBHA Resin (0.5–0.7 meq./g titer, Nova Biochem, Lajolla, Calif., USA), 5 g (0.64 mmole/g, 3.2 mmole) is swollen by shaking with 60 mL dimethylformamide, then the resin is drained and washed with two 60 mL portions of diemthyl formamide. The 9-fluorenylmethoxycarbonyl group (Fmoc) is then removed by treating the resin with 60 mL of 20% piperidine/dimethylformamide for 20 minutes, followed by four 60 mL washes of the resin with dimethylformamide (TNBS: positive). Fmoc-Val-OH (2.17 g, 6.4 mmole) and 2.43 g (6.4 mmole) O-benzotriazole-1-yl-N,N,N',N'-tetramethyluronium hexafluorophosphate (HBTU) in 150 mL dimethylformamide are treated with 32 mL (12.8 mmole) N-methylmorpholine at 0° C. for 10 minutes, then the mixture is added to the resin peptide and the mixture agitated by shaking at ambient temperature for about 1.3 hour. The resin was drained, then washed with three 150 mL portions of dimethylformamide.(TNBS: negative). The resin was washed with two portions of diethyl ether and dried overnight; the weigh gain from the coupling was 0.88 g, implying the addition of 2.75 mmole Val). The synthesis was continued by sequentially removing Fmoc (as above) and coupling (as above) with 5.6 moles each of Fmoc-Asp (OtBu), Fmoc-Gln(Trt), Fmoc-Leu, Fmoc-Leu, Fmoc-Lys (Boc), Fmoc-Arg(Pmc), Fmoc-Leu, and Fmoc-Trp(Boc), using 5.6 molar equivalents of HBTU, 11.2 mmole N-methylmorpholine, and 50 mL dimethylformamide in each coupling. The final weight gain was 5.8 g. An aliquot was cleaved to provide the title peptide retaining the Fmoc but with side chains deprotected, of 86A % purity. LC-MS: 1390.6; calc. 1390.8).

Step 2
Fmoc-cyclo(Lys-Asp)Lys-Glu(OtBu)-Arg(Pmc)-Val-Asp-OH (SEQ ID NO: 42)

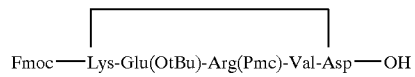

Method A: Solid Phase Synthesis
a. Sequence Assembly: Synthesis of Fmoc-Lys(Alloc)-Glu(OtBu)-Arg(Pmc)-Val-Asp(OAllyl)-Chlorotrityl resin (SEQ ID NO: 43).

Coupling of Fmoc-Asp(OAllyl)-OH to 15 g 1% crosslink chlorotrityl resin of 1.05 meq/g loading (total 15.75 mmole) was accomplished using 7.89 g (18.9 mmole) of Fmoc-Asp (OAllyl)-OH, 82 g (39.9 mmole) of benzotriazolyloxy-tris [pyrrolidino]-phosphonium hexafluoroacetate (PyBOP) and 10.2 g (78.8 mmole) of diisopropylethyl amine in 150 mL dichloromethane. The mixture was agitated by shaking, then drained and the resin washed using three 150 mL portions dichloromethane/methanol/diisopropylethylamine (17:2:1), followed by three 150 mL portions dichloromethane. The resin was sampled for a TNBS test, which was negative. The N-terminal 9-fluorenylmethoxycarbonyl group was removed by treating the Fmoc-protected resin-bound amino acid with 150 mL 5% piperidine in dichloromethane-dimethylformamide (1:1) for 10 minutes followed by 150 mL 20% piperidine in dimethylformamide for 30 minutes. The resin-bound amino acid was washed as described above. Fmoc-Val-OH, Fmoc-Arg(Pmc)-OH (10% aliquot removed after this step), Fmoc-Glu(OtBu)-OH and Fmoc-Lys(c-Alloc)-OH are each coupled in the same fashion and using the same sequence of events, however using three to five dimethylformamide washes in place of three dichloromethane washes before TNBS testing. No double couplings are required. The final resin bound peptide was washed with 150 mL tetrahydrofuran and 150 mL diethyl ether, then was dried under vacuum to afford 27.23 g.

b. Allyl and Alloc Removal for Lys¹⁸ and Asp²²: Synthesis of Fmoc-Lys-Glu(OtBu)-Arg(Pmc)-Val-Asp-Chlorotrityl resin (SEQ ID NO: 44).

A 10 g portion of the Fmoc-(Lys-Alloc)-Glu(OtBu)-Arg (Pmc)-Val-Asp(OAllyl)-chlorotrityl resin (SEQ ID NO: 43) prepared above was swollen in a shaker with 100 mL dimethylsulfoxide/dimethylformamide/dichlormethane (1:1:0.2 v/v/v) for 20 minutes, then the resin was gently drained. A partial solution of 2.9 g tetrakistriphenylphosphine palladium (0) in 240 mL dimethylsulfoxide/dimethylformamide (1:1, v:v) was added, followed by 60 mL dichloromethane and 16.2 g (150 mmole) N-methylanaline, then the mixture was agitated by shaking for 2 hours. The resin was drained and washed with 3 100 mL portions dichloromethane. The resin was then swollen with 100 mL dimethylsulfoxide/dimethylformamide (1:1 v:v), then gently drained and used directly in Lys¹⁸-Asp²³ cyclization.

c. Formation of Lys¹⁸-Asp²² Lactam Bridge: Synthesis of Fmoc-cyclo(Lys-Asp)Lys-Glu(OtBu)-Arg(Pmc)-Val-Asp-Chlorotrityl resin (SEQ ID NO: 45).

Resin Peptide from the above example is treated with 5.2 g (10 mmole) benzotriazolyloxy-tris[pyrrolidino]-phosphonium hexafluoroacetate (PyBOP) and 2.6 g (20 mmole) diisopropylethyl amine in 100 mL dimethylsulfoxide/dimethylformamide (1:1 v:v), and the mixture agitated for 4 hours. The resin was drained and washed with 3 100 mL portions of dimethylformamide, then an aliquot of drained resin was withdrawn for TNBS testing (negative). The resin was washed with 100 mL each of tetrahydrofuran and diethyl ether, then was dried under vacuum.

d. Resin Cleavage and Product Isolation of Fmoc-cyclo(Lys-Asp)Lys-Glu(OtBu)-Arg(Pmc)-Val-Asp-OH (SEQ ID NO: 42).

The resin peptide from the above Lys$^{18}$-Asp$^{22}$ lactam bridge formation example was treated in a shaker with 130 mL acetic acid/dichloromethane/2,2,2-trifluoroethanol (1:8:1)for 20 minutes. The liquid portion was drawn from the resin and treated with 500 mL methyl tert butyl ether and 100 mL diethyl ether, and the mixture centrifuged. The supernatent was removed, and to the residue was added diethyl ether, followed by centrifugation. The supernatant was removed and the residue was dried overnight to afford 2.77 g of a yellow solid (MS: 1172; 41% stoich. yield, crude). This was purified by flash chromatography (85:15 to 60:40 dichloromethane : methanol) to afford 1 g Fmoc-cyclo (Lys-Asp)Lys-Glu(OtBu)-Arg(Pmc)-Val-Asp-OH (15% yield based on resin) with 85A % purity.

Method B: Synthesis in Solution a. Sequence Assembly

Synthesis of Boc-Asp(OAllyl)-OBzl

In a 3 neck, 3 L flask charged with 1,1-dimethylethoxycarbonyl-(L)-aspartic acid benzyl ester (50 g, 154.5 mmol), dichloromethane (96 mL), allyl alcohol (9.43 g, 162.3 mmol) and 4-N,N-dimethylamino pyridine (10 mg) at ambient temperature. The reaction mixture is cooled to 8° C., and a solution of dicyclohexylcarbodiimide (32 g, 154.5 mmol) in dichloromethane (100 mL) is added over 1.5 hours at 8–11° C. As the dicyclohexylcarbodiimide solution is added, dicyclohexyl urea precipitates. The reaction mixture is stirred for 2 hours at 11–12° C., at which point HPLC shows no starting material. The dicyclohexyl urea is filtered off and the filtrate is concentrated. The oily residue is taken up in methyl-t-butyl ether (250 mL), and the solution is filtered to remove residual dicyclohexyl urea, washed with 30 mL 0.2N hydrochloric acid, 30 mL water, 20 mL saturated aqueous sodium bicarbonate, 30 mL water, and two 50 mL portions of brine, dried (magnesium sulfate), filtered, and concentrated to give 55.88 g of Boc-(L)Asp (OAllyl)-OBzl as an oil. ($M_{calc}$ 363.4; $M+1_{obsvd}$ 364).

Synthesis of HCl-Asp(OAllyl)-OBzl

A solution of Boc-Asp(OAllyl)-OBzl (110.5 g, 302.7 mmol) in 500 mL ethyl acetate in a 3 neck, 3 L flask with a mechanical stirrer is cooled to 5° C. and hydrogen chloride gas is bubbled through the reaction mixture for 2.5 hours during which time the reaction temperature reaches about 22° C. HPLC shows no starting material. Nitrogen is bubbled into the solution overnight, resulting in formation of a white precipitate which is collected by filtration and washed with 100 mL of ethyl acetate. The residue is dried under vacuum to afford 84 g HCl.Asp(OAllyl)-OBzl as a white crystalline (microscopy) solid. ($M_{calc}$ 263; $M+1_{obsvd}$ 264).

Synthesis of Boc-Val-Asp(OAllyl)-Obzl (SEQ ID NO: 33)

To a solution of Boc-Val-OH (25.4 g, 116.7 mmol) in ethyl acetate (85 mL) is added hydroxybenzotriazole hydrate (16.55 g, 122.5 mmol) in dimethylformamide (122.3 mL). The mixture is cooled to 5° C. and a solution of dicyclo-hexylcarbodiimide (25.2 g, 122.5 mmol) in ethyl acetate (58.7 mL) is added over 1 hour during which time the temperature rises to about 18° C. and dicyclohexyl urea precipitates. Cooling is ceased and the mixture is stirred for 2 hours and a solution of HCl.H$_2$N-Asp(OAllyl)-OBzl (35 g, 116.7 mmol) in 189 mL of dimethylformamide is added over 25 minutes. N-methylmorpholine (12.8 mL) is added slowly and over 0.5 hours to attain a reaction mixture pH of 7 and the mixture is stirred at ambient temperature for 36 hours. The reaction mixture is filtered to remove dicyclohexyl urea, the filtrate is diluted with methyl-t-butyl ether, stirred for 2 hours, then refiltered. The filtrate is washed with 100 mL water, 100 mL 0.5M aqueous citric acid, 100 mL water, 100 mL saturated aqueous, sodium bicarbonate, 100 mL brine, dried (magnesium sulfate), filtered, and concentrated to give 41.3 g of Boc-Val-Asp(OAllyl)-OBzl as an oil. ($M_{calc}$ 462; $M+1_{obsvd}$ 463).

Synthesis of HCl.Val-Asp(OAllyl)-OBzl (SEQ ID NO: 34)

A 2–4° C. solution of Boc-Val-Asp(OAllyl)-OBzl (31.7 g, 68.5 mmol) in ethyl acetate (300 mL) is charged with hydrogen chloride gas for 2 hours. Cooling is ceased and the mixture is stirred for 48 hours. Nitrogen is rigorously bubbled into the solution for 1 hour. The reaction mixture is concentrated on the rotary evaporator to give 38.3 g of a white solid, which is crystallized from ethyl acetate to afford 24.2 g of HCl.Val-Asp(OAllyl)-OBzl. ($M_{calc}$ 362 $M+1_{obsvd}$ 363).

Synthesis of Fmoc-Arg(Pmc)-Val-Asp(OAllyl)-OBzl (SEQ ID NO: 35)

In a 3 neck, 3 L flask equipped with a mechanical stirrer is placed 17.25 g (26 mmol) Fmoc-Arg(Pmc) and 300 mL acetonitrile and the mixture is stirred at ambient temperature until a clear solution is obtained. Benzotriazolyloxy-tris [pyrrolidino]-phosphonium hexafluoroacetate (PyBOP) is added, the solution cooled to 2° C., and 2.6 g (26 mmol) of N-methylmorpholine is added, forming a white tar. Dimethylformamide (52 mL) is added slowly until the tar dissolves, and the mixture is stirred at 3° C. for 30 minutes. A solution of HCl.Val-Asp(OAllyl)-OBzl) (10.4 g, 26 mmol) in 39 mL of dimethylformamide is added over 20 minutes at 2–3° C., followed by N-methylmorpholine (7.5 mL) to attain pH 7. Cooling is ceased, and the mixture is stirred for 2.5 hours. The mixture is then diluted with 250 mL water and 250 mL ethyl acetate. The ethyl acetate layer is removed and washed with water (2×100 mL) and brine (2×100 mL) and concentrated to afford a white solid which is crystallized from 175 mL ethyl acetate to give 18.5 g Fmoc-Arg(Pmc)-Val-Asp (OAllyl)-OBzl (95A %). The ethyl acetate filtrate is concentrated and the gummy residue triturated with ethyl acetate to afford an additional 3.12 g of product. ($M_{calc}$ 1007; $M+1_{obsvd}$ 1008).

Synthesis of Arg(Pmc)-Val-Asp(OAllyl)-OBzl (SEQ ID NO: 36)

To a solution of Fmoc-Arg(Pmc)-Val-Asp(OAllyl)-OBzl (SEQ ID NO: 35) (16 g, 15.9 mmol) in dichloromethane (267 mL) is added piperidine (23 g, 27 mmol, 26.7 mL) at ambient temperature. The reaction is stirred 2.5 hours and then is washed with water (2×60 mL) and brine (2×60 mL), dried (magnesium sulfate), filtered, and concentrated to give a semi-solid. The semi-solid is taken up in 400 mL ethyl acetate and the solution is left standing for three days and then is filtered. The filtrate is washed with water (2×60 mL), dried (magnesium sulfate), filtered and concentrated to afford 23.5 g of product contaminated with piperidine-benzofulvene adduct (MS analysis). The solid is dissolved in 400 mL ethyl acetate, filtered, washed with water (2×60 mL), dried (magnesium sulfate), and concentrated to afford a solid which is dried overnight under vacuum to afford 12.55 g of Arg(Pmc)-Val-Asp(OAll)-OBzl (SEQ ID NO: 36)as a white solid. ($M_{calc}$ 784 $M+1_{obsvd}$ 785).

Synthesis of Fmoc-Glu(OtBu)-Arg(Pmc)-Val-Asp(OAllyl)-OBzl (SEQ ID NO: 37)

To a solution of Fmoc-Glu(tBu) (6.73 g, 15.8 mmol) and benzotriazolyloxy-tris[pyrrolidino]-phosphonium hexafluoroacetate (PyBOP, 8.18 g, 15.8 mmol) in 105 mL acetonitrile at 2° C. is added N-methylmorpholine (1.58 g, 15.8 mmol) and the reaction mixture is stirred at 2–4° C. for 30 minutes. A solution of L)Arg(Pmc)-Val-Asp(OAllyl)-OBzl (12.4 g, 15.8 mmole) in 70 mL acetonitrile is added at 2° .C over 20 minutes. N-methylmorpholine is then added to achieve pH 7. Cooling is ceased, and the mixture is allowed to warm to ambient temperature, then stirred is continued for a total of 3 hours. The milky reaction mixture is filtered (slow) and the white residue is dried in the filter overnight to afford 10.8 g of Fmoc-Glu(OBut)-Arg(Pmc)-Val-Asp(Allyl)-OBzl. The filtrate is concentrated to give a gum, which is taken up in 30 mL acetonitrile and allowed to stand for 48 hours, producing an additional 3.45 g of product. The total yield of Fmoc-Glu(OtBu)-Arg(Pmc)-Val-Asp(OAllyl)-OBzl is 14.3 g. ($M_{calc}$ 1192; $M+1_{obsvd}$ 1192.4)

Synthesis of Glu(OtBu)-Arg(Pmc)-Val-Asp(OAllyl)-OBzl (SEQ ID NO: 38)

To a solution of Fmoc-Glu(OBut)-Arg(Pmc)-Val-Asp (OAllyl)-OBzl (SEQ ID NO: 37) (12.3 g, 10.3 mmol) in 105 mL of dichloromethane is added piperidine (3.5 g, 41.3 mmol) at ambient temperature. The mixture is stirred 2 hours, then diluted with heptane, concentrated to half volume, and left standing in the freezer overnight. The liquor is decanted from the oily residue, which is then taken up in dichloromethane. The solution is washed with 0.5M aqueous citric acid, water, and brine, dried (magnesium sulfate), filtered, and concentrated. The crude solid is triturated twice with heptane and filtered to give 9.0 g of Glu(OtBu)-(L)Arg (Pmc)-Val-Asp(OAllyl)-OBzl as a white powder. ($M_{calc}$ 970.2; $M+1_{obsvd}$ 971).

Synthesis of Fmoc-Lys(Alloc)-Glu(OtBu)-Arg(Pmc)-Val-Asp(OAllyl)-Obzl (SEQ ID NO: 39)

A suspension of Fmoc-Lys(Alloc) (4.2 g, 9.3 mmol) and benzotriazolyloxy-tris[pyrrolidino]-phosphonium hexafluoroacetate (PyBOP, 4.8 g, 9.3 mmol) in 69 mL acetonitrile at 5° C. is treated with N-methylmorpholine (0.94 g, 9.3 mmol), resulting in formation of a solution which is stirred at 5° C. for 30 minutes. A suspension of Glu(OtBu)-Arg (Pmc)-Val-Asp(Allyl)-OBzl (9 g, 9.3 mmole) in 52 mL acetonitrile is added, causing the reaction mixture to become cloudy white. N-methylmorpholine is added until the reaction mixture is at pH 7, then the mixture is allowed to warm to ambient temperature and stir for 1.33 hours. The mixture is filtered and the solid residue is washed with acetonitrile (2×40 mL) and dried overnight under vacuum with a nitrogen bleed to give 12.8 g of an off-white crusty solid which is triturated with 200 mL methyl-t-butyl ether, collected by filtration and dried under vacuum to afford 9.7 g of Fmoc-Lys(Alloc)-Glu(OtBu)-Arg(Pmc)-Val-Asp(OAllyl)-OBzl. (SEQ ID NO: 39) ($M_{calc}$ 1404.7; $M+1_{obsvd}$ 1406).

b. Alloc and Allyl removal From $Lys^{18}$ and $Asp^{22}$: Synthesis of Fmoc-Lys-Glu(OtBu)-Arg(Pmc)-Val-Asp-Obzl (SEQ ID NO: 40) A 3 neck 1 L flask equipped with mechanical stirrer and nitrogen flow is charged at ambient temperature with 167 mL of dichloromethane and 1.37 g (1.18 mmol, 0.2 eq.) of Pd(PPh$_3$)$_4$. Nitrogen is bubbled into the orange solution for 2 minutes, then a solution of 8.3 g (5.91 mmol, 1.0 eq.) of Fmoc-Lys(Alloc)-Glu(OtBu)-Arg (Pmc)-Val-Asp(OAllyl)-OBzl in 66.4 mL of dimethylformamide is added, followed by 13.3 g, (124 mmol, 21 eq.) of methylaniline. The solution is stirred at ambient temperature for 1 hour. The mixture is diluted with 700 mL of methyl-t-butyl ether which causes a solid to form. The suspension is stirred for 1 hour and filtered. The solid residue is triturated with 200 mL of methyl-t-butyl ether, filtered and dried to obtain 5.0 g of a pale yellow solid. The filtrate yields 1.1 g of a second crop as a pale yellow solid for a total yield of 6.1 g of Fmoc-Lys-Glu(OtBu)-Arg(Pmc)-Val-Asp-Obzl (SEQ ID NO: 40). ($M_{calc}$ 1280.6; $M+1_{obsvd}$ 1281).

c. $Lys^{18}$-$Asp^{22}$ Lactam Bridge Formation: Synthesis of Fmoc-cyclo(Lys-Asp)Lys-Glu(OtBu)-Arg(Pmc)-Val-Asp-Obzl (SEQ ID NO: 41)

In a 3 neck 1 L flask is dissolved 6.0 g, (4.69 mmol) of Fmoc-Lys-Glu(OtBu)-Arg(Pmc)-Val-Asp-OBzl (SEQ ID NO: 40) in 300 mL of dimethyl formamide at room temperature under nitrogen and 3.44 g, (6.61 mmol, 1.41 eq.) of benzotriazolyloxy-tris[pyrrolidino]-phosphonium hexafluoroacetate (PyBOP), 0.89 g, (6.57 mmol, 1.40 eq.) of hydroxybenzotriazole hydrate, and 1.73 g, (13.4 mmol; 2.85 eq.) of diisopropylethyl amine are added. The orange solution is stirred for 1 hour at ambient temperature, then is diluted with 300 mL of water which results in formation of an oily residue. The cloudy liquor (containing mostly impurities) is decanted. The oily residue is stirred overnight with 100 mL of water, affording a crusty solid which is collected by filtration, giving 4.2 g of a pale yellow solid. The filtrate affords a 1.0 g of a second crop as a yellow solid, for a total yield of 5.2 g of Fmoc-cyclo(Lys-Asp)Lys-Glu (OtBu)-Arg(Pmc)-Val-Asp-OBzl. ($M_{calc}$ 1262 $M+1_{obsvd}$ 1262.5).

d. Removal of Benzyl Ester: Synthesis Fmoc-cyclo(Lys-Asp)Lys-Glu(OtBu)-Arg(Pmc)-Val-Asp-OH (SEQ ID NO: 42)

A solution of 5.9 g (4.7 mmol) of Fmoc-cyclo(Lys-Asp) Lys-Glu-Arg-Val-Asp-OBzl (SEQ ID NO: 41) in 25 mL dimethylformamide is treated with 5.9 g charcoal and filtered, and then is treated with 0.59 g 10% Pd/C and placed under 50 psig of hydrogen on a Parr apparatus. After 1.5 hours, the mixture is filtered, treated again with charcoal, refiltered, and recharged with 0.59 g 10% Pd/C and exposed to 50 psig hydrogen for an additional 2 hours. The mixture is filtered and the filtrate is diluted with 50 mL water and extracted with three 200 mL portions of methylene chloride. The combined methylene chloride extracts are concentrated to afford 1.2 g of Fmoc-cyclo(Lys-Asp)Lys-Glu(OtBu)-Arg (Pmc)-Val-Asp-OH (SEQ ID NO: 42), an oil. ($M_{calc}$ 1171; $M+1_{obsvd}$ 1172.3).

3. Purification

A 400 mg sample of Fmoc-cyclo(Lys-Asp)Lys-Glu (OtBu)-Arg(Pmc)-Val-Asp-OH (SEQ ID NO: 42) is dissolved in 10 mL 1:1 trifluoroethanol/isopropanol. The sample is injected in two 5 mL slugs onto a preparative HPLC column (Microsorb MV C18, 300Ang, 8u, 41.4×250 mm) equilibrated with 55% B (A=0.1% vl/vl aqueous trifluoroacetic acid; B=v/v 75% acetonitrile/25% isopropanol with 0.1% trifluoroacetic acid). The charge is eluted at 70 mL/minute in a gradient of 55% B to 65% B over 30 minutes, 65%B to 95% B over 1 minute, followed by isocratic column washing with 95%B for 10 minutes. Effluent is monitored using UV at 210 nM. Fractions with purity of 93.5A % or higher are pooled and concentrated by rotary evaporation. Lyophilization of the residue affords 200 mg of Fmoc-cyclo(Lys-Asp)Lys-Glu-Arg(Pmc)-Val-Asp-OH (SEQ ID NO: 42) ($M_{calc}$ 1171; $M+1_{obsvd}$ 1172.6).

Step 3

(SEQ ID NO: 29)

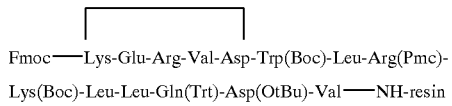
Fmoc—Lys-Glu-Arg-Val-Asp-Trp(Boc)-Leu-Arg(Pmc)-
Lys(Boc)-Leu-Leu-Gln(Trt)-Asp(OtBu)-Val—NH-resin Fmoc-[Trp$^{23}$(Boc), Arg$^{25}$(Pmc), Lys$^{26}$(Boc), Leu$^{27}$, Gln$^{29}$ (Trt)]HPTH(23–31)-chlorotrityl resin (1 g, 0.185 mmole) was swollen in 10 mL dimethylformamide with shaking agitation for 30 minutes, then was drained and treated with 10 mL 20% piperidine/dimethylformamide (v/v) with shaking agitation for 30 minutes. The resin was drained and washed with 3 20 mL portions of dimethylformamide. A solution of 240 mg (0.205 mmole. 1.1 eq.) of Fmoc-cyclo (Lys$^{18}$-Asp$^{22}$)Lys-Glu(OtBu)-Arg(Pmc)-Val-Asp-OH, 312 mg (0.6 mmole. 3 eq.) benzotriazolyloxy-tris[pyrrolidino]-phosphonium hexafluoroacetate (PyBOP), and 156 mg (1.2 mmole, 6 eq) diisopropylethyl amine in 10 mL dimethylformamide was added and the mixture agitated for 16 h. The resin was drained and washed with three 20 mL portions of dimethylformamide (TNBS positive) and retreated with of Fmoc-cyclo(Lys$^{18}$-Asp$^{22}$)Lys-Glu(OtBu)-Arg(Pmc)-Val-Asp-OH/PyBOP/iPr2NEt a second time for 16 h, then the resin was drained and washed with three 10 mL portions dimethylformamide (TNBS: negative). An aliquot of the title peptide was cleaved from the resin as described in Step 2, Method A using Reagent K, to afford the side-chain deprotected peptide fragment. (LC-MS: $M_{calc}$ 2001; $M_{obsvd}$ 2000.5). The remainder was used in Step 4.

Step 4

(SEQ ID NO: 30)

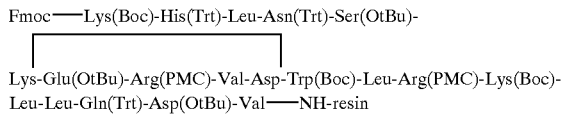
Fmoc—Lys(Boc)-His(Trt)-Leu-Asn(Trt)-Ser(OtBu)-
Lys-Glu(OtBu)-Arg(PMC)-Val-Asp-Trp(Boc)-Leu-Arg(PMC)-Lys(Boc)-
Leu-Leu-Gln(Trt)-Asp(OtBu)-Val—NH-resin The desired resin-bound peptide was prepared by removal of the Fmoc protecting group from 1.38 g (0.244 mmole based upon titer at Trp$^{23}$) of the resin-bound peptide of Step 3 as per Step 1, followed by sequential cycling of Fmoc removal and coupling with 0.5 mmole each of Fmoc-Ser (OtBu)-OH, Fmoc-Asn(Trt)-OH, Fmoc-Leu-OH, Fmoc-His (Trt)-OH, and Fmoc-Lys(Boc)-OH as per Step 1, using 190 mg (0.5 mmole) of O-benzotriazole-1-yl-N,N,N',N'-tetramethyluronium hexafluorophosphate (HBTU) and 2 mmole) of N-methylmorpholine in 25 mL dimethylformamide. The couplings were performed at ambient temperature over about 1 hour. The final resin peptide was washed with 25 mL portions of dimethylformamide, tetrahydrofuran, and diethyl ether and dried under vacuum (1.93 g) An aliquot of the title peptide was cleaved from the resin as described below (Reagent K), to afford the side-chain deprotected peptide fragment (LC-MS: $M_{calc}$ 2579.4; $M_{obsvd}$ 2580.7) of 52A % purity.

Step 5

Fmoc-Ala-Val-Ser(OtBu)-Glu(OtBu)-Ile-Gln(Trt)-Leu-Nle-His(Trt)-Asn(Trt)-Leu-Gly-OH (SEQ ID NO: 31)

The title peptide is prepared by coupling 2.65 g (5 mmole) Fmoc-Leu-OH to 5 g (3 mmole) of 1% crosslink Gly-2-chlorotrityl resin of 0.6 meq/g with 3.9 g (7.5 mmole) benzotriazolyloxy-tris[pyrrolidino]-phosphonium hexafluoroacetate (PyBOP), 1.94 g (15 mmole) diisopropyl ethyl amine in 50 mL dimethylformamide/tetrahydrofuran (v/v) using shaking agitation, for 0.5 hours. The resin was drained, then washed with five portions of dimethylformamide/tetrahydrofuran and one portion of methanol (Ninhydrin: negative). The resin was washed once with dimethylformamide, then treated twice with 60 mL 20% piperidine/dimethylformamide for 15 minutes each time, with three 60 mL portions of dimethylformamide and one 60 mL portion of methanol between each treatment. After the second such treatment, the ninhydrin was highly positive. This cycle was repeated, using a single 0.5 hour piperidine dimethylformamide treatment in each subsequent case, and using 2.5 molar equivalents each of Fmoc-Asn(Trt), Fmoc-His(Trt), Fmoc-Nle, Fmoc-Leu, Fmoc-Gln(Trt), Fmoc-Ile, Fmoc Glu(OtBu), Fmoc-Ser(OtBu), Fmoc-Val, and Fmoc-Ala, along with 2.5 molar equivalents each of PyBOP and diisopropylethyl amine. The resin peptide was cleaved by shaking with 100 mL acetic acid/trifluoroethylene/and dichloromethane (1:1:8) for 1 hour. The liquid was drained from the resin, and the resin was washed with 200 mL dichloromethane; then wash was combined with the main portion of the liquid. This was evaporated sequentially from hexane, ethyl acetate, and isopropanol. To the residue was triturated with diethyl ether, then dried (overnight, vacuum) to afford 2.24 g of the title peptide (HPLC: 83A % pure). The resin was retreated under cleavage conditions a second time and the liquid treated as after the first cleavage, to finally afford 2.75 g of a second crop of the title peptide, for a total yield of 4.95 g (2.1 mmole, 70% yld. from resin). [LC-MS ($M_{calc}$ 1514.8; $M_{obsvd}$ 1514.7]. This material was used as obtained in Step 6.

Step 6

(SEQ ID NO: 32)

Fmoc—Ala-Val-Ser(OtBu)-Glu(OtBu)-Ile-Gln(Trt)-Leu-Nle-His(Trt)-
Asn(Trt)-Leu-Gly-Lys(Boc)-His(Trt)-Leu-Asn(Trt)-Ser(OtBu)-
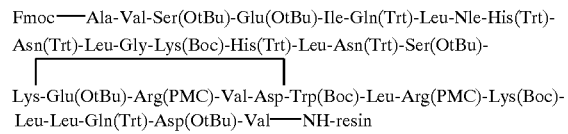
Lys-Glu(OtBu)-Arg(PMC)-Val-Asp-Trp(Boc)-Leu-Arg(PMC)-Lys(Boc)-
Leu-Leu-Gln(Trt)-Asp(OtBu)-Val—NH-resin The peptide prepared in Step 5 (900 mg, 0.114 mmole) was swollen in 15 mL dimethylformamide for 40 minutes with shaking agitation, then the resin was drained and treated with 15 mL 20% piperidine/dimethylformamide (v/v) for 45 minutes. The resin was drained and washed with three 30 mL portions dimethylformamide (resin TNBS test: positive). To this was added 15 mL dimethylformamide, 775 mg (0.33 mmole, 2.7 molar eq. based upon titer at position 23) Fmoc-[Ala$^1$, Ser$^3$(OtBu), Glu$^4$(OtBu), Gln$^6$(Trt), His$^9$ (Trt), Asn$^{10}$(Trt)Nle$^8$]hPTH(1–12) (from Step 4), 151 mg (0.29 mmole, 0.21 molar eq.) benzotriazolyloxy-tris [pyrrolidino]-phosphonium hexafluoroacetate (PyBOP), 39 mg (0.25 mole) hydroxybenzotriazole hydrate and 75 mg (0.58 mmole) diisopropylethyl amine, and the mixture agitated by shaking for 3 days. The resin was drained, washed with three 30 mL portions of dimethylformamide, (TNBS, mix of sl. positive and negative beads), then treated with 15 mL 20% piperidine/dimethylformamide (v/v), drained, and washed with three 15 mL portions each of dimethylformamide, tetrahydrofuran, and diethyl ether, then dried and deprotected and cleaved from resin as per Step 7.

Step 7

(SEQ ID NO: 1)

Ala-Val-Ser-Glu-Ile-Gln-Leu-Nle-His-Asn-Leu-Gly-Lys-His-Leu-Asn-
⌐                                             ¬
Ser-Lys-Glu-Arg-Val-Asp-Trp-Leu-Arg-Lys-Leu-Leu-Gln-Asp-Val—NH$_2$

The resin peptide from Step 6 was treated to remove Fmoc on Ala$^1$ as per Step 1 Method A, then simultaneously cleaved and deprotected in a 33/2/2/1/2 mixture of trifluoroacetic acid, phenol, thioanisole, ethanedithiol, and water (Reagent K total dilution 10 mL/g resin-peptide) for 3 hours. The resin was drained and product was precipitated from the filtrate by adding the reaction mixture to cold t-butylmethyl ether (50 mL/g resin-peptide). The mixture was left standing for 15 minutes, then was centrifuged (2000 rpm, 5 minutes). The liquid was decanted and the remaining solid was washed with diethyl ether, the mixture supernatant was separated by centrifugation and the supernatant removed. The resulting solid was stirred in 0.1% aqueous trifluoroacetic acid (6 mL/g resin peptide) for 1 hour to ensure complete removal of acid sensitive groups. The solution was lyophilized to afford 414 mg of the title peptide (37A % pure, 26.3% pure by wt/wt, 26.3% yield from Trp$^{23}$) as a white solid. (LC-MS: M$_{calc}$ 3632.0; M+1$_{obsvd}$ 3633.4).

Step 8
Purification

One gram of the material prepared above is dissolved in 10 mL water and the solution is injected onto a 2"×25 cm preparative HPLC (10 micron, 120A or 300A) pre-equilibrated with 75/5/20 0.1% aq. trifluoroacetic acid (A)/0.1% trifluoroacetic acid in acetonitrile (B)/isopropanol (C). The column is eluted at 115 mL per minute with a gradient 75A/5B/20C to 60A/20B/20C over 30 minutes, then flushed with 30%A, 60%B, 20%C and re-equilibrated with 75A/5B/20C. Effluent is monitored using UV detection at 280nm. Fractions containing the title peptide of ca. 75 area percent purity are combined and concentrated on a rotary evaporator ~35° C. The concentrated aqueous solution is pumped onto the same preparative column and rerun through the same 30 minute gradient. Fractions containing the title peptide at 90A % or greater area percent purity are combined and concentrated on a rotary evaporator at ~35° C. The concentrated solution is then pumped onto the preparative column which had been pre-equilibrated with 75% 0.1M aq. ammonium acetate (adjusted to pH 6 with acetic acid) (D)/15% acetonitrile (E)/10% isopropanol (C). The column is eluted at 115 mL/minute with 75D/15E/10C to 60D/30E/10C over 30 minutes, then flushed with 30D/60E/20C. Fractions containing the title peptide of 95A % or higher percent area purity are combined and lyophilized, providing purified product as the solid, acetate salt (1 g crude gives ca. 100–200 mg @ ca. 95A % purity). At each stage, fractions are analyzed for content and purity using analytical HPLC on a C18 column (4.6 mm×25 cm, 5 micron, 120A or 300A) in a gradient of 25–40%B (A=0.1% Trifluoroacetic acid/water; B=0.1% trifluoroacetic acid acetonitrile) over 30 minutes using a flow of 1 mL/minute and UV monitoring at 220 nm.

What is claimed is:

1. A method for preparing a peptide having the formula:

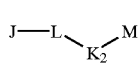
IIA wherein
J, L, and M are linear peptide fragments, and
$K_2$ is a cyclic peptide fragment;
this method comprising the steps of:
(1) preparing

by sequential attachment of suitably protected amino acid residues to a resin to provide:

III where

is a suitable peptide synthesis resin and M is a peptide fragment;

(2) preparing separately by conventional peptide synthesis an N-terminally protected cyclic peptide of formula IV

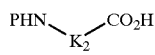
IV wherein P is a suitable amine protecting group, (3) coupling peptide III with peptide IV to provide a peptide of formula V

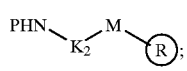
V (4) either (a) preparing peptide fragments J and L as a single peptide of formula VI

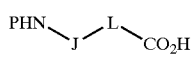
VI then removing the protecting group from the N-terminus of peptide V and coupling peptide VI to the thus deprotected derivative of peptide V to provide a peptide of formula VII

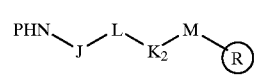
VII or (b) removing the protecting group from the N-terminus of peptide V and adding the protected individual amino acid elements of peptides J and L sequentially to the thus deprotected derivative of peptide V (using appropriate deprotection between individual additions), or (c) separately preparing either or both of peptides J and L as peptide fragments and coupling these peptide fragments to the growing peptide starting with the peptide of formula V; and (5) cleaving the resulting peptide from the resin, deprotecting said peptide and recovering it from the reaction medium.

2. The method of claim 1, wherein the peptide of formula IIA is a cyclic peptide compound of the formula $X-A_{10}-A_{11}-A_{12}-A_{13}-A_{14}-A_{15}-A_{16}-A_{17}-A_{18}-A_{19}-A_{20}-A_{21}-A_{22}-A_{23}-A_{24}-A_{25}-A_{26}-A_{27}-Y$ wherein X is selected from the group consisting of
(a) $R_{1a}-A_0-A_1-A_2-A_3-A_4-A_5-A_6-A_7-A_8-A_9-$,
(b) $R_{1a}-A_2-A_3-A_4-A_5-A_6-A_7-A_8-A_9-$,
(c) $R_{1b}-A_3-A_4-A_5-A_6-A_7-A_8-A_9-$,
(d) $R_{1a}-A_4-A_5-A_6-A_7-A_8-A_9-$,
(e) $R_{1a}-A_5-A_6-A_7-A_8-A_9-$,
(f) $R_{1a}-A_6-A_7-A_8-A_9-$,
(g) $R_{1a}-A_7-A_8-A_9-$,
(h) $R_{1a}-A_8-A_9-$,
(i) $R_{1a}-A_9-$, and
(j) $R_{1a}-$;

Y is selected from the group consisting of
(a) $-R_3$,
(b) $-A_{28}-R_3$,
(c) $-A_{28}-A_{29}-R_3$,
(d) $-A_{28}-A_{29}-A_{30}-R_3$,
(e) $-A_{28}-A_{29}-A_{30}-A_{31}-R_3$,
(f) $-A_{28}-A_{29}-A_{30}-A_{31}-A_{32}-R_3$,
(g) $-A_{28}-A_{29}-A_{30}-A_{31}-A_{32}-A_{33}-R_3$, and
(h) $-A_{28}-A_{29}-A_{30}-A_{31}-A_{32}-A_{33}-A_{34}-R_3$;

$R_{1a}$ is H, alkyl, aralkyl or —$COR_2$;
$R_{1b}$ is $R_{1a}$ or a group of formula

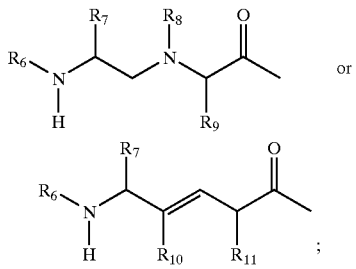

$R_2$ is alkyl, alkenyl, alkynyl, aryl or aralkyl;
$R_3$ is a group of formula $A_{35}$—$OR_4$ or $A_{35}$—$NR_4R_5$;
$R_4$ and $R_5$ are independently H or lower alkyl;
$R_6$ and $R_9$ are independently H or alkyl;
$R_7$ is alkyl;
$R_8$ is H, alkyl or $COR_2$;
$R_{10}$ is H or halogen;
$R_{11}$ is alkyl or aralkyl;
m is 1, 2 or 3;
n is 3 or 4;
$A_0$ is absent or a peptide of from one to six amino acid residues;
$A_1$ is Ser, Ala, Gly or D-Pro, or an equivalent amino acid;
$A_2$ is Ala, Val or Gly, or an equivalent amino acid;
$A_3$ is Ala, Ser, Gly or D-Pro, or an equivalent amino acid;
$A_4$ is Glu, Ala or Gly, or an equivalent amino acid;
$A_5$ is Ile, His, Ala or Gly, or an equivalent amino acid thereof;
$A_6$ is Ala, Gln, Gly or D-Pro, or an equivalent amino acid thereof;
$A_7$ is Ala, Leu, Gly, or an equivalent amino acid thereof;
$A_8$ is Leu, Nle, Gly or D-Pro, or an equivalent amino acid thereof;
$A_9$ is His, Ala, D-Pro or Gly, or an equivalent amino acid thereof;
$A_{10}$ is Ala, Asn, Asp, Cys, homo-Cys, Glu, Gly, Lys, Orn, Ser, Thr, D-Pro, —$NHCH[(CH_2)_mNH_2]CO$— or —$NHCH[(CH_2)_nCO_2H]CO$—;
$A_{11}$ is Ala, Gly, Leu or Lys, or an equivalent amino acid thereof;
$A_{12}$ is Ala or Gly, or an equivalent amino acid thereof;
$A_{13}$ is Ala, Asn, Asp, Cys, homo-Cys, Glu, Gly, Lys, Orn, Ser, Thr, —$NHCH[(CH_2)_mNH_2]CO$— or —$NHCH[(CH_2)_nCO_2H]CO$—;
$A_{14}$ is Ala, Asn, Asp, Cys, homo-Cys, Glu, Gly, His, Lys, Orn, Ser, Thr, D-Pro, —$NHCH[(CH_2)_mNH_2]CO$— or —$NHCH[(CH_2)_nCO_2H]CO$—;
$A_{15}$ is Ala, Gly, Ile, D-Pro or Leu, or an equivalent amino acid thereof;
$A_{16}$ is Asn, Ala, Gly, D-Pro or Gln, or an equivalent amino acid thereof;
$A_{17}$ is Ala, Asn, Asp, Cys, homo-Cys, Glu, Gly, Lys, Orn, Ser, Thr, D-Pro, —$NHCH[(CH_2)_mNH_2]CO$— or —$NHCH[(CH_2)_nCO_2H]CO$—;
$A_{18}$ is Asp, Cys, homo-Cys, Glu, His, Leu, Lys, Orn, Nle, Ser, Thr, —$NHCH[(CH_2)_mNH_2]CO$— or —$NHCH[(CH_2)_nCO_2H]CO$—;

$A_{19}$ is Arg or Glu, or an equivalent amino acid thereof;
$A_{20}$ is Arg or an equivalent amino acid thereof;
$A_{21}$ is Arg, Asp, Cys, homo-Cys, Glu, Lys, Orn, Ser, Thr, Val, —$NHCH[(CH_2)_mNH_2]CO$— or —$NHCH[(CH_2)_nCO_2H]CO$—;
$A_{22}$ is Asp, Cys, homo-Cys, Glu, His, Lys, Orn, Phe, Ser, Thr, —$NHCH[(CH_2)_mNH_2]CO$— or —$NHCH[(CH_2)_nCO_2H]CO$—;
$A_{23}$ is Leu, Phe or Trp, or an equivalent amino acid thereof;
$A_{24}$ is Leu or an equivalent amino acid thereof;
$A_{25}$ is Arg, Asp, Cys, homo-Cys, Glu, His, Lys, Orn, D-Pro, Ser, Thr, —$NHCH[(CH_2)_mNH_2]CO$— or —$NHCH[(CH_2)_nCO_2H]CO$—;
$A_{26}$ is Asp, Cys, homo-Cys, Glu, His, Lys, Orn, Ser, Thr, —$NHCH[(CH_2)_mNH_2]CO$— or —$NHCH[(CH_2)_nCOH]CO$—;
$A_{27}$ is Leu or Lys, or an equivalent amino acid thereof;
$A_{28}$ is Ile or Leu, or an equivalent amino acid thereof;
$A_{29}$ is Ala, Asp, Cys, homo-Cys, Glu, Gln, Lys, Orn, Ser, Thr, —$NHCH[(CH_2)_mNH_2]CO$— or —$NHCH[(CH_2)_nCO_2H]CO$—;
$A_{30}$ is Asp, Cys, homo-Cys, Glu, Gly, Lys, Orn, Ser, Thr, —$NHCH[(CH_2)_mNH_2]CO$— or —$NHCH[(CH_2)_nCO_2H]CO$—;
$A_{31}$ is Ile, Leu or Val, or an equivalent amino acid thereof;
$A_{32}$ is His, or an equivalent amino acid thereof;
$A_{33}$ is Asn or Thr, or an equivalent amino acid thereof; and
$A_{34}$ is Ala or Phe, or an equivalent amino acid thereof;
$A_{35}$ is absent or a peptide of from 1 to 4 amino acids; and
the side chains of one of the following pairs of amino acid residues, $A_{10}$ and $A_{14}$, $A_{14}$ and, $A_{17}$ and $A_{21}$, $A_{18}$ and $A_{22}$, $A_{21}$ and $A_{25}$, and $A_{25}$ and $A_{29}$ are linked through an amide, ester, disulfide or lanthionine bond to form a bridge.

3. A method according to claim 1 for preparing cyclo ($Lys^{18}$-$Asp^{22}$)[$Ala^1$,$Nle^8$,$Lys^{18}$,$Asp^{22}$,$Leu^{27}$]hPTH(1-31) $NH_2$ (SEQ ID NO: 1) which method comprises the steps of (a) preparing the resin-bound peptide A:
Fmoc-Tri(Boc)-Leu-Arg(Pmc)-Lys(Boc)-Leu-Leu-Gln(Trt)-Asp)(OtBu)-Val-NH-resin (SEQ ID NO: 28) (A);

(b) preparing the cyclic peptide (SEQ ID NO: 42) (B)

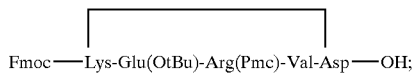

(c) coupling peptide A of step (a) with peptide B of step (b) to form intermediate peptide AB (SEQ ID NO: 29) (AB)

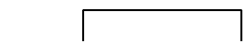

Fmoc—Lys-Glu-Arg-Val-Asp-Trp(Boc)-Leu-Arg(Pmc)-
Lys(Boc)-Leu-Leu-Gln(Trt)-Asp(OtBu)-Val—NH-resin;

(d) sequentially adding to peptide AB Ser(OtBu), Asn(Trt), Leu, His(Trt), and Lys(Boc) to form intermediate resin-bound peptide C:

(SEQ ID NO: 30) (C)

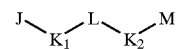

Fmoc——Lys(Boc)-His(Trt)-Leu-Asn(Trt)-Ser(OtBu)-

Lys-Glu(OtBu)-Arg(PMC)-Val-Asp-Trp(Boc)-Leu-Arg(PMC)-Lys(Boc)-Leu-Leu-Gln(Trt)-Asp(OtBu)-Val——NH-resin;

(e) preparing peptide D:
Fmoc-Ala-Val-Ser(OtBu)-Glu(OtBu)-Ile-Gln(Trt)-Leu-Nle-His(Trt)-Asn(Trt)-Leu-Gly-OH (SEQ ID NO: 31) (D);

(f) deprotecting the N-terminus of peptide C and coupling the thus deprotected derivative of peptide C with peptide D to form resin-bound peptide E:

(SEQ ID NO: 32) (E)

Fmoc——Ala-Val-Ser(OtBu)-Glu(OtBu)-Ile-Gln(Trt)-Leu-Nle-His(Trt)-Asn(Trt)Leu-Gly-Lys(Boc)-His(Trt)-Leu-Asn(Trt)-Ser(OtBu)-

Lys-Glu(OtBu)-Arg(PMC)-Val-Asp-Trp(Boc)-Leu-Arg(PMC)-Lys(Boc)-Leu-Leu-Gln(Trt)-Asp(OtBu)-Val——NH-resin; and (g) cleaving the resulting peptide from the resin, deprotecting said peptide and recovering the title deprptected peptide, cyclo(Lys$^{18}$-Asp$^{22}$)[Ala$^1$,Nle$^8$,Lys$^{18}$,Asp$^{22}$,Leu$^{27}$]hPTH(1-31)NH$_2$, (SEQ ID NO: 1) from the reaction medium.

4. A peptide intermediate for the method of claim 3, selected from the group consisting of:
cyclo(Lys$^{18}$-Asp$^{22}$)Fmoc-Lys-Glu(OtBu)-Arg(Pmc)-Val-Asp-Trp(Boc)-Leu-Arg(Pmc)-Lys(Boc)-Leu-Leu-Gln(Trt)-Asp(OtBu)-Val-NH-resin (SEQ ID NO: 29),
Cyclo(Lys$^{18}$-Asp$^{22}$)Fmoc-Lys(Boc)-His(Trt)-Leu-Asn(Trt)-Ser(OtBu)-Lys-Glu(OtBu)-Arg(Pmc)-Val-Asp-Trp(Boc)-Leu-Arg(Pmc)-Lys(Boc)-Leu-Leu-Gln(Trt)-Asp(OtBu)-Val-NH-resin (SEQ ID NO: 30),
Cyclo(Lys$^{18}$-Asp$^{22}$)Fmoc-Ala-Val-Ser(OtBu)-Glu(OtBu)-Ile-Gln(Trt)-Leu-Nle-His(Trt)-Asn(Trt)-Leu-Gly-Lys(Boc)-His(Trt)-Leu-Asn(Trt)-Ser(OtBu)-Lys-Glu(OtBu)-Arg(Pmc)-Val-Asp-Trp(Boc)-Leu-Arg(Pmc)-Lys(Boc)-Leu-Leu-Gln(Trt)-Asp(OtBu)-Val-NH-resin (SEQ ID NO: 32),
Fmoc-cyclo(Lys-Asp)Lys-Glu(OtBu)-Arg(Pmc)-Val-Asp-Obzl (SEQ ID NO: 41),
Fmoc-cyclo(Lys-Asp)Lys-Glu(OtBu)-Arg(Pmc)-Val-Asp-OH (SEQ ID NO: 42), and
Fmoc-cyclo(Lys-Asp)Lys-Glu(OtBu)-Arg(Pmc)-Val-Asp-Chlorotrityl resin (SEQ ID NO: 43).

5. A peptide intermediate for the method of claim 3, selected from the group consisting of:
Fmoc-Trp(Boc)-Leu-Arg(Pmc)-Lys(Boc)-Leu-Leu-Gln(Trt)-Asp(OtBu)-Val-NH-resin (SEQ ID NO: 28),
Fmoc-Ala-Val-Ser(OtBu)-Glu(OtBu)-Ile-Gln(Trt)-Leu-Nle-His(Trt)-Asn(Trt)-Leu-Gly-OH (SEQ ID NO: 31),
Boc-Val-Asp(OAllyl)-Obzl (SEQ ID NO: 33),
HCl.Val-Asp(OAllyl)-Obzl (SEQ ID NO: 34),
Fmoc-Arg(Pmc)-Val-Asp(OAllyl)-Obzl (SEQ ID NO: 35),
Arg(Pmc)-Val-Asp(OAllyl)-Obzl (SEQ ID NO: 36),
Fmoc-Glu(OtBu)-Arg(Pmc)-Val-Asp(OAllyl)-Obzl (SEQ ID NO: 37),
Glu(OtBu)-Arg(Pmc)-Val-Asp(OAllyl)-Obzl (SEQ ID NO: 38),
Fmoc-Lys(Alloc)-Glu(OtBu)-Arg(Pmc)-Val-Asp(OAllyl)-Obzl (SEQ ID NO: 39),
Fmoc-Lys-Glu(OtBu)-Arg(Pmc)-Val-Asp-Obzl (SEQ ID NO: 40),
Fmoc-Lys(Alloc)-Glu(OtBu)-Arg(Pmc)-Val-Asp(OAllyl)-Chlorotrityl resin (SEQ ID NO: 43), and
Fmoc-Lys-Glu(OtBu)-Arg(Pmc)-Val-Asp-Chlorotrityl resin (SEQ ID NO: 44).

6. A method for preparing a peptide having the formula:

$$J\underset{K_1}{\diagdown}L\underset{K_2}{\diagdown}M \qquad \text{IIB}$$

wherein

J, L, and M are linear peptide fragments
$K_1$ is a cyclic peptide fragment, and
$K_2$ is a cyclic peptide fragment;
this method comprising the steps of:

(1) preparing

by sequential attachment of suitably protected amino acid residues to a resin to provide:

III

where

is a suitable peptide synthesis resin and M is a peptide fragment;

(2) preparing separately by conventional peptide synthesis an N-terminally protected cyclic peptide fragment of formula IV

IV

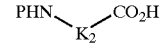

wherein P is a suitable amine protecting group, (3) Coupling peptide III with peptide IV to provide a peptide of formula V

V

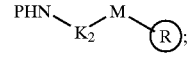

(4) (a) preparing separately N-terminal protected cyclic peptide of formula VIII

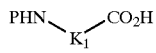   VIII wherein

P is a suitable amine protecting group, by conventional peptide synthesis procedures;

(b) preparing a peptide of formula IX

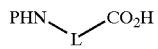   IX (c) removing the protecting group from the N-terminus of peptide V and coupling peptide fragment IX with the thus deprotected derivative of peptide V to provide a peptide of formula X

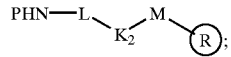   X and (d) removing the protecting group from the N-terminus of peptide X and coupling cyclic peptide VIII with the thus deprotected derivative of peptide X to provide a peptide of formula XI

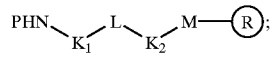   XI (e) preparing peptide XII

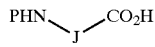   XII (f) removing the protecting group from the N-terminus of peptide XI and coupling peptide XII with the thus deprotected derivative of peptide XI; and (5) cleaving the resulting peptide from the resin, deprotecting said peptide and recovering said deprotected peptide from the reaction medium.

7. The method of claim 6, wherein the peptide of formula IIB is a cyclic peptide compound of the formula X—$A_{10}$—$A_{11}$—$A_{12}$—$A_{13}$—$A_{14}$—$A_{15}$—$A_{16}$—$A_{17}$—$A_{18}$—$A_{19}$—$A_{20}$—$A_{21}$—$A_{22}$—$A_{23}$—$A_{24}$—$A_{25}$—$A_{26}$—$A_{27}$—Y wherein X is selected from the group consisting of
(a) $R_{1a}$—$A_0$—$A_1$—$A_2$—$A_3$—$A_4$—$A_5$—$A_6$—$A_7$—$A_8$—$A_9$—,
(b) $R_{1a}$—$A_2$—$A_3$—$A_4$—$A_5$—$A_6$—$A_7$—$A_8$—$A_9$—,
(c) $R_{1b}$—$A_3$—$A_4$—$A_5$—$A_6$—$A_7$—$A_8$—$A_9$—,
(d) $R_{1a}$—$A_4$—$A_5$—$A_6$—$A_7$—$A_8$—$A_9$—,
(e) $R_{1a}$—$A_5$—$A_6$—$A_7$—$A_8$—$A_9$—,
(f) $R_{1a}$—$A_6$—$A_7$—$A_8$—$A_9$—,
(g) $R_{1a}$—$A_7$—$A_8$—$A_9$—,
(h) $R_{1a}$—$A_8$—$A_9$—,
(i) $R_{1a}$—$A_9$—, and
(j) $R_{1a}$;

Y is selected from the group consisting of
(a) —$R_3$,
(b) —$A_{28}$—$R_3$,
(c) —$A_{28}$—$A_{29}$—$R_3$,
(d) —$A_{28}$—$A_{29}$—$A_{30}$—$R_3$,
(e) —$A_{28}$—$A_{29}$—$A_{30}$—$A_{31}$—$R_3$,
(f) —$A_{28}$—$A_{29}$—$A_{30}$—$A_{31}$—$A_{32}$—$R_3$,
(g) —$A_{28}$—$A_{29}$—$A_{30}$—$A_{31}$—$A_{32}$—$A_{33}$—$R_3$, and
(h) —$A_{28}$—$A_{29}$—$A_{30}$—$A_{31}$—$A_{32}$—$A_{33}$—$A_{34}$—$R_3$;

$R_{1a}$ is H, alkyl, aralkyl or —$COR_2$;

$R_{1b}$ is $R_{1a}$ or a group of formula

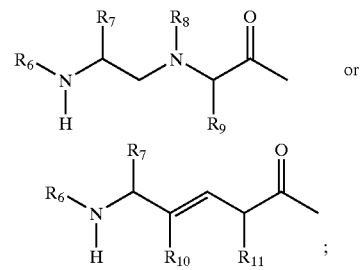

$R_2$ is alkyl, alkenyl, alkynyl, aryl or aralkyl;

$R_3$ is a group of formula $A_{35}$—$OR_4$ or $A_{35}$—$NR_4R_5$;

$R_4$ and $R_5$ are independently H or lower alkyl;

$R_6$ and $R_9$ are independently H or alkyl;

$R_7$ is alkyl;

$R_8$ is H, alkyl or $COR_2$;

$R_{10}$ is H or halogen;

$R_{11}$ is alkyl or aralkyl;

m is 1, 2 or 3;

n is 3 or 4;

$A_0$ is absent or a peptide of from one to six amino acid residues;

$A_1$ is Ser, Ala, Gly or D-Pro, or an equivalent amino acid;

$A_2$ is Ala, Val or Gly, or an equivalent amino acid;

$A_3$ is Ala, Ser, Gly or D-Pro, or an equivalent amino acid;

$A_4$ is Glu, Ala or Gly, or an equivalent amino acid;

$A_5$ is Ile, His, Ala or Gly, or an equivalent amino acid thereof;

$A_6$ is Ala, Gln, Gly or D-Pro, or an equivalent amino acid thereof;

$A_7$ is Ala, Leu, Gly, or an equivalent amino acid thereof;

$A_8$ is Leu, Nle, Gly or D-Pro, or an equivalent amino acid thereof;

$A_9$ is His, Ala, D-Pro or Gly, or an equivalent amino acid thereof;

$A_{10}$ is Ala, Asn, Asp, Cys, homo-Cys, Glu, Gly, Lys, Orn, Ser, Thr, D-Pro, —NHCH[$(CH_2)_m NH_2$]CO— or —NHCH[$(CH_2)_n CO_2H$]CO—;

$A_{11}$ is Ala, Gly, Leu or Lys, or an equivalent amino acid thereof;

$A_{12}$ is Ala or Gly, or an equivalent amino acid thereof;

$A_{13}$ is Ala, Asn, Asp, Cys, homo-Cys, Glu, Gly, Lys, Orn, Ser, Thr, —NHCH[$(CH_2)_m NH_2$]CO— or —NHCH[$(CH_2)_n CO_2H$]CO—;

$A_{14}$ is Ala, Asn, Asp, Cys, homo-Cys, Glu, Gly, His, Lys, Orn, Ser, Thr, D-Pro, —NHCH[$(CH_2)_m NH_2$]CO— or —NHCH[$(CH_2)_n CO_2H$]CO—;

$A_{15}$ is Ala, Gly, Ile, D-Pro or Leu, or an equivalent amino acid thereof;

$A_{16}$ is Asn, Ala, Gly, D-Pro or Gln, or an equivalent amino acid thereof;

$A_{17}$ is Ala, Asn, Asp, Cys, homo-Cys, Glu, Gly, Lys, Orn, Ser, Thr, D-Pro, —NHCH[$(CH_2)_m$NH$_2$]CO— or —NHCH[$(CH_2)_n$CO$_2$H]CO—;

$A_{18}$ is Asp, Cys, homo-Cys, Glu, His, Leu, Lys, Orn, Nle, Ser. Thr, —NHCH[$(CH_2)_m$NH$_2$]CO— or —NHCH[$(CH_2)_n$CO$_2$H]CO—;

$A_{19}$ is Arg or Glu, or an equivalent amino acid thereof;

$A_{20}$ is Arg or an equivalent amino acid thereof;

$A_{21}$ is Arg, Asp, Cys, homo-Cys, Glu, Lys, Orn, Ser, Thr, Val, —NHCH[$(CH_2)_m$NH$_2$]CO— or —NHCH[$(CH_2)_n$CO$_2$H]CO—;

$A_{22}$ is Asp, Cys, homo-Cys, Glu, His, Lys, Orn, Phe, Ser, Thr, —NHCH[$(CH_2)_m$NH$_2$]CO— or —NHCH[$(CH_2)_n$CO$_2$H]CO—;

$A_{23}$ is Leu, Phe or Trp, or an equivalent amino acid thereof;

$A_{24}$ is Leu or an equivalent amino acid thereof;

$A_{25}$ is Arg, Asp, Cys, homo-Cys, Glu, His, Lys, Orn, D-Pro, Ser, Thr, —NHCH[$(CH_2)_m$NH$_2$]CO— or —NHCH[$(CH_2)_n$CO$_2$H]CO—;

$A_{26}$ is Asp, Cys, homo-Cys, Glu, His, Lys, Orn, Ser, Thr, —NHCH[$(CH_2)_m$NH$_2$]CO— or —NHCH[$(CH_2)_n$CO$_2$H]CO—;

$A_{27}$ is Leu or Lys, or an equivalent amino acid thereof;

$A_{28}$ is Ile or Leu, or an equivalent amino acid thereof;

$A_{29}$ is Ala, Asp, Cys, homo-Cys, Glu, Gln, Lys, Orn, Ser, Thr, —NHCH[$(CH_2)_m$NH$_2$]CO— or —NHCH[$(CH_2)_n$CO$_2$H]CO—;

$A_{30}$ is Asp, Cys, homo-Cys, Glu, Gly, Lys, Orn, Ser, Thr, —NHCH[$(CH_2)_m$NH$_2$]CO— or —NHCH[$(CH_2)_n$CO$_2$H]CO—;

$A_{31}$ is Ile, Leu or Val, or an equivalent amino acid thereof;

$A_{32}$ is His, or an equivalent amino acid thereof;

$A_{33}$ is Asn or Thr, or an equivalent amino-acid thereof; and $A_{34}$ is Ala or Phe, or an equivalent amino acid thereof;

$A_{35}$ is absent or a peptide of from 1 to 4 amino acids; and the side chains of one of the following pairs of amino acid residues, $A_{13}$ and $A_{17}$, and $A_{26}$ and $A_{30}$ are linked through an amide, ester, disulfide or lanthionine bond to form a bridge; provided, however, that (a) when the side chains of amino acid acid residues $A_{13}$ and $A_{17}$ are linked to form a bridge, then the side chains of at least one of the following pairs of amino acid residues $A_{21}$ and $A_{25}$ and $A_{25}$ and $A_{29}$ are also linked to form a bridge, and (b) when the side chains of amino acid residues $A_{26}$ and $A_{30}$ are linked to form a bridge, then the side chains of at least one of the following pairs of amino acid residues, $A_{10}$ and $A_4$, $A_{14}$ and $A_{18}$, $A_{17}$ and $A_{21}$, and $A_{18}$ and $A_{22}$ are also linked to form a bridge.

\* \* \* \* \*

SEQUENCE LISTING

```
<160> NUMBER OF SEQ ID NOS: 46

<210> SEQ ID NO 1
<211> LENGTH: 31
<212> TYPE: PRT
<213> ORGANISM: Artificial Sequence
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond"
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 1

Ala Val Ser Glu Ile Gln Leu Xaa His Asn Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 2
<211> LENGTH: 31
<212> TYPE: PRT
<213> ORGANISM: Artificial Sequence
<220> FEATURE:
```

```
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 2

Ala Ala Ser Glu Ile Gln Leu Xaa His Asn Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 3
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      COHN2."

<400> SEQUENCE: 3

Ala Val Ala Glu Ile Gln Leu Xaa His Asn Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 4
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      COHN2."

<400> SEQUENCE: 4

Ala Val Ser Ala Ile Gln Leu Xaa His Asn Leu Gly Lys His Leu Asn
 1               5                  10                  15
```

```
Ser Lys Glu Arg Val Asp Trp Leu Arg Lys Leu Leu Gln Asp Val
            20                  25                  30

<210> SEQ ID NO 5
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 5

Ala Val Ser Glu Ala Gln Leu Xaa His Asn Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 6
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 6

Ala Val Ser Glu Ile Ala Leu Xaa His Asn Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 7
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
```

```
<222> LOCATION: (31)
<223> OTHER INFORMATION: "This C-terminal amino acid is an amide, i.e.,
      CONH2."

<400> SEQUENCE: 7

Ala Val Ser Glu Ile Gln Ala Xaa His Asn Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 8
<211> LENGTH: 31
<212> TYPE: PRT
<213> ORGANISM: Artificial Sequence
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 8

Ala Val Ser Glu Ile Gln Leu Ala His Asn Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 9
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 9

Ala Val Ser Glu Ile Gln Leu Xaa His Ala Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 10
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
```

```
        position 18 and Asp at position 22 are linked by
        an amide bond."
<220> FEATURE:
<221> NAME/KEY: PEPTIDE
<222> LOCATION: (31)
<223> OTHER INFORMATION: "This C-terminal amino acid is an amide, i.e.,
        CONH2."

<400> SEQUENCE: 10

Ala Val Ser Glu Ile Gln Leu Xaa His Asn Ala Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 11
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
        position 18 and Asp at position 22 are linked by
        an amide bond."
<220> FEATURE:
<221> NAME/KEY: PEPTIDE
<222> LOCATION: (31)
<223> OTHER INFORMATION: "This C-terminal amino acid is an amide, i.e.,
        CONH2."

<400> SEQUENCE: 11

Ala Val Ser Glu Ile Gln Leu Xaa His Asn Leu Ala Lys His Leu Asn
 1               5                  10                  15

Ser Lys Glu Arg Val Asp Trp Leu Arg Lys Leu Leu Gln Asp Val
            20                  25                  30

<210> SEQ ID NO 12
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
        position 18 and Asp at position 22 are linked by
        an amide bond."
<220> FEATURE:
<221> NAME/KEY: PEPTIDE
<222> LOCATION: (31)
<223> OTHER INFORMATION: "This C-terminal amino acid is an amide, i.e.,
        CONH2."

<400> SEQUENCE: 12

Ala Val Ser Glu Ile Gln Leu Xaa His Asn Leu Gly Ala His Leu Asn
 1               5                  10                  15

Ser Lys Glu Arg Val Asp Trp Leu Arg Lys Leu Leu Gln Asp Val
            20                  25                  30

<210> SEQ ID NO 13
<211> LENGTH: 31
<212> TYPE: PRT
<213> ORGANISM: Artificial Sequence
```

```
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptides: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 13

Ala Val Ser Glu Ile Gln Leu Xaa His Asn Leu Gly Lys Ala Leu Asn
 1               5                  10                  15

Ser Lys Glu Arg Val Asp Trp Leu Arg Lys Leu Leu Gln Asp Val
            20                  25                  30

<210> SEQ ID NO 14
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptides: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 14

Ala Val Ser Glu Ile Gln Leu Xaa His Asn Leu Gly Lys His Ala Asn
 1               5                  10                  15

Ser Lys Glu Arg Val Asp Trp Leu Arg Lys Leu Leu Gln Asp Val
            20                  25                  30

<210> SEQ ID NO 15
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 15

Ala Val Ser Glu Ile Gln Leu Xaa His Asn Leu Gly Lys His Leu Ala
 1               5                  10                  15
```

```
Ser Lys Glu Arg Val Asp Trp Leu Arg Lys Leu Leu Gln Asp Val
            20                  25                  30

<210> SEQ ID NO 16
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (13)..(17)
<223> OTHER INFORMATION: "Synthetic Peptide: The side chain of Lys at
      position 13 and Asp at position 17 are linked by
      an amide bond."
<220> FEATURE:
<221> NAME/KEY: PEPTIDE
<222> LOCATION: (18)..(22)
<223> OTHER INFORMATION: "Synthetic Peptide: The side chain of Lys at
      position 18  and Asp at position 22 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 16

Ala Val Ser Glu Ile Gln Leu Xaa His Asn Leu Gly Lys His Leu Asn
 1               5                  10                  15

Asp Lys Glu Arg Val Asp Trp Leu Arg Lys Leu Leu Gln Asp Val
            20                  25                  30

<210> SEQ ID NO 17
<211> LENGTH: 31
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chain of Lys at
      position 18 and Asp at position 22 are linked by
      an amide bond."
<220> FEATURE:
<221> NAME/KEY: PEPTIDE
<222> LOCATION: (26)..(30)
<223> OTHER INFORMATION: "Synthetic Peptide: The side chain of Lys at
      position 26 and Asp at position 30 are linked by
      an amide bond."
<220> FEATURE:
<221> NAME/KEY: PEPTIDE
<222> LOCATION: (31)
<223> OTHER INFORMATION: "This C-terminal amino acid is an amide, i.e.,
      CONH2."

<400> SEQUENCE: 17

Ala Val Ser Glu Ile Gln Leu Xaa His Asn Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 18
<211> LENGTH: 34
<212> TYPE: PRT
<213> ORGANISM: Artificial Sequence
<220> FEATURE:
```

```
<221> NAME/KEY: MOD_RES
<222> LOCATION: (8)
<223> OTHER INFORMATION: Nle
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (34)
<223> OTHER INFORMATION: "This C-terminal amino acid is an amide, i.e.,
      COHN2."

<400> SEQUENCE: 18

Ala Val Ser Glu Ile Gln Leu Xaa His Asn Leu Gly Lys His Leu Asn
 1               5                  10                  15

Ser Lys Glu Arg Val Asp Trp Leu Arg Lys Leu Leu Gln Asp Val His
            20                  25                  30

Asn Phe

<210> SEQ ID NO 19
<211> LENGTH: 34
<212> TYPE: PRT
<213> ORGANISM: Artificial Sequence
<220> FEATURE:
<221> NAME/KEY: MOD_RES
<222> LOCATION: (8)
<223> OTHER INFORMATION: Nle
<220> FEATURE:
<221> NAME/KEY: PEPTIDE
<222> LOCATION: (13)..(17)
<223> OTHER INFORMATION: "Synthetic Peptide: The side chain of Lys at
      position 13 and Asp at position 17 are linked by
      an amide bond."
<220> FEATURE:
<221> NAME/KEY: PEPTIDE
<222> LOCATION: (18)..(22)
<223> OTHER INFORMATION: "Synthetic Peptide: The side chain of Lys at
      position 18 and Asp at position 22 are linked by
      an amide bond."
<220> FEATURE:
<221> NAME/KEY: PEPTIDE
<222> LOCATION: (34)
<223> OTHER INFORMATION: "This C-terminal amino acid is an amide, i.e.,
      CONH2."

<400> SEQUENCE: 19

Ala Val Ser Glu Ile Gln Leu Xaa His Asn Leu Gly Lys His Leu Asn
 1               5                  10                  15

Asp Lys Glu Arg Val Asp Trp Leu Arg Lys Leu Leu Gln Asp Val His
            20                  25                  30

Asn Phe

<210> SEQ ID NO 20
<211> LENGTH: 34
<212> TYPE: PRT
<213> ORGANISM: Artificial Sequence
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (34)
<223> OTHER INFORMATION: "This C-terminal amino acid is an amide, i.e.,
      CONH2."
```

```
<400> SEQUENCE: 20

Ala Val Ser Glu His Gln Leu Leu His Asp Lys Gly Lys Ser Ile Gln
 1               5                   10                  15

Asp Lys Arg Arg Arg Asp Phe Leu His His Leu Ile Ala Glu Ile His
            20                  25                  30

Thr Ala

<210> SEQ ID NO 21
<211> LENGTH: 34
<212> TYPE: PRT
<213> ORGANISM: Artificial Sequence
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22  are linked by
      an amide bond."
<220> FEATURE:
<221> NAME/KEY: PEPTIDE
<222> LOCATION: (34)
<223> OTHER INFORMATION: "This C-terminal amino acid is an amide, i.e.,
      CONH2."

<400> SEQUENCE: 21

Ala Val Ser Glu His Gln Leu Leu His Asp Lys Gly Lys Ser Ile Gln
 1               5                   10                  15

Asp Lys Arg Arg Arg Asp Leu Leu Glu Lys Leu Leu Glu Lys Leu His
            20                  25                  30

Thr Ala

<210> SEQ ID NO 22
<211> LENGTH: 28
<212> TYPE: PRT
<213> ORGANISM: Artificial Sequence
<220> FEATURE:
<221> NAME/KEY: PEPTIDE
<222> LOCATION: (12)..(16)
<223> OTHER INFORMATION: "Synthetic Peptide: The side chains of Lys at
      position 12 and Asp at position 16 are linked by
      an amide bond."
<220> FEATURE:
<221> NAME/KEY: PEPTIDE
<222> LOCATION: (28)
<223> OTHER INFORMATION: "This C-terminal amino acid is an amide, i.e.,
      CONH2."
<220> FEATURE:
<221> NAME/KEY: MOD_RES
<222> LOCATION: (2)
<223> OTHER INFORMATION: Nle

<400> SEQUENCE: 22

Leu Xaa His Asn Leu Gly Lys His Leu Asn Ser Lys Glu Arg Val Asp
 1               5                   10                  15

Trp Leu Arg Lys Leu Leu Gln Asp Val His Asn Phe
            20                  25

<210> SEQ ID NO 23
<211> LENGTH: 28
<212> TYPE: PRT
<213> ORGANISM: Artificial Sequence
<220> FEATURE:
<221> NAME/KEY: PEPTIDE
<222> LOCATION: (12)..(16)
<223> OTHER INFORMATION: "Synthetic Peptide: The side chains of Lys at
      position 12 and Asp at position 16 are linked by
      an amide bond."
<220> FEATURE:
<221> NAME/KEY: PEPTIDE
```

```
<222> LOCATION: (28)
<223> OTHER INFORMATION: "This C-terminal amino acid is an amide, i.e.,
      CONH2."

<400> SEQUENCE: 23

Leu Leu His Asp Lys Gly Lys Ser Ile Gln Asp Lys Arg Arg Arg Asp
 1               5                  10                  15

Phe Leu His His Leu Ile Ala Glu Ile His Thr Ala
             20                  25

<210> SEQ ID NO 24
<211> LENGTH: 28
<212> TYPE: PRT
<213> ORGANISM: Artificial Sequence
<220> FEATURE:
<221> NAME/KEY: MOD_RES
<222> LOCATION: (2)
<223> OTHER INFORMATION: Nle
<220> FEATURE:
<221> NAME/KEY: PEPTIDE
<222> LOCATION: (7)..(11)
<223> OTHER INFORMATION: "Synthetic Peptide: The side chains of Lys at
      position 7 and Asp at position 11 are lined by an
      amide bond."
<220> FEATURE:
<221> NAME/KEY: PEPTIDE
<222> LOCATION: (12)..(16)
<223> OTHER INFORMATION: "Synthetic Peptide: The side chains of Lys at
      position 12 and Asp at position 16 are linked by
      amide bonds."
<220> FEATURE:
<221> NAME/KEY: PEPTIDE
<222> LOCATION: (28)
<223> OTHER INFORMATION: "This C-terminal amino acid is an amide, i.e.,
      CONH2."

<400> SEQUENCE: 24

Leu Xaa His Asn Leu Gly Lys His Leu Asn Asp Lys Glu Arg Val Asp
 1               5                  10                  15

Trp Leu Arg Lys Leu Leu Gln Asp Val His Asn Phe
             20                  25

<210> SEQ ID NO 25
<211> LENGTH: 28
<212> TYPE: PRT
<213> ORGANISM: Artificial Sequence
<220> FEATURE:
<221> NAME/KEY: MOD_RES
<222> LOCATION: (2)
<223> OTHER INFORMATION: Nle
<220> FEATURE:
<221> NAME/KEY: PEPTIDE
<222> LOCATION: (12)..(16)
<223> OTHER INFORMATION: "Synthetic Peptide: The side chains of Lys at
      position 12 and Asp at position 16 are linked by
      an amide bond."
<220> FEATURE:
<221> NAME/KEY: PEPTIDE
<222> LOCATION: (20)..(24)
<223> OTHER INFORMATION: "Synthetic Peptide: The side chains of Lys at
      position 20 and Asp at position 24 are linked by
      an amide bond."
<220> FEATURE:
<221> NAME/KEY: PEPTIDE
<222> LOCATION: (28)
<223> OTHER INFORMATION: "This C-terminal amino acid is an amide, i.e.,
      CONH2."

<400> SEQUENCE: 25

Leu Xaa His Asn Leu Gly Lys His Leu Asn Ser Lys Glu Arg Val Asp
 1               5                  10                  15
```

```
Trp Leu Arg Lys Leu Leu Gln Asp Val His Asn Phe
            20                  25

<210> SEQ ID NO 26
<211> LENGTH: 34
<212> TYPE: PRT
<213> ORGANISM: Artificial Sequence

<400> SEQUENCE: 26

Ser Val Ser Glu Ile Gln Leu Met His Asn Leu Gly Lys His Leu Asn
  1               5                  10                  15

Ser Met Glu Arg Val Glu Trp Leu Arg Lys Lys Leu Gln Asp Val His
            20                  25                  30

Asn Phe

<210> SEQ ID NO 27
<211> LENGTH: 34
<212> TYPE: PRT
<213> ORGANISM: Artificial Sequence

<400> SEQUENCE: 27

Ala Val Ser Glu His Gln Leu Leu His Asp Lys Gly Lys Ser Ile Gln
  1               5                  10                  15

Asp Leu Arg Arg Arg Phe Phe Leu His His Leu Ile Ala Glu Ile His
            20                  25                  30

Thr Ala

<210> SEQ ID NO 28
<211> LENGTH: 9
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Trp(BOC)
<220> FEATURE:
<221> NAME/KEY: PEPTIDE
<222> LOCATION: (3)
<223> OTHER INFORMATION: product=Arg(PMC)
<220> FEATURE:
<221> NAME/KEY: PEPTIDE
<222> LOCATION: (4)
<223> OTHER INFORMATION: product=Lys(BOC)
<220> FEATURE:
<221> NAME/KEY: PEPTIDE
<222> LOCATION: (7)
<223> OTHER INFORMATION: product=Gln(Trt)
<220> FEATURE:
<221> NAME/KEY: PEPTIDE
<222> LOCATION: (8)
<223> OTHER INFORMATION: product=Asp(OtBu)
<220> FEATURE:
<221> NAME/KEY: PEPTIDE
<222> LOCATION: (9)
<223> OTHER INFORMATION: Synthetic Peptide Other- "This C-terminal amino
      acid is bonded via an amide bond to Rink Amide
      MBHA resin."

<400> SEQUENCE: 28

Trp Leu Arg Lys Leu Leu Gln Asp Val
  1               5

<210> SEQ ID NO 29
<211> LENGTH: 14
<212> TYPE: PRT
<213> ORGANISM: Artificial Sequence
<220> FEATURE:
<221> NAME/KEY: PEPTIDE
```

```
<222> LOCATION: (1)
<223> OTHER INFORMATION: FMOC-Lys
<220> FEATURE:
<221> NAME/KEY: PEPTIDE
<222> LOCATION: (1)..(5)
<223> OTHER INFORMATION: "Synthetic Peptides: The side chains of Lys at
      position 1 and Asp at position 5 are linked by an
      amide bond."
<220> FEATURE:
<221> NAME/KEY: PEPTIDE
<222> LOCATION: (2)
<223> OTHER INFORMATION: Glu(OtBu)
<220> FEATURE:
<221> NAME/KEY: PEPTIDE
<222> LOCATION: (3)
<223> OTHER INFORMATION: Arg(PMC)
<220> FEATURE:
<221> NAME/KEY: PEPTIDE
<222> LOCATION: (1)..(5)
<223> OTHER INFORMATION: "Synthetic Peptide: The side chains of Lys at
      position 1 and Asp at position 5 are linked by an
      amide bond."
<220> FEATURE:
<221> NAME/KEY: PEPTIDE
<222> LOCATION: (6)
<223> OTHER INFORMATION: Trp(BOC)
<220> FEATURE:
<221> NAME/KEY: PEPTIDE
<222> LOCATION: (8)
<223> OTHER INFORMATION: Arg(PMC)
<220> FEATURE:
<221> NAME/KEY: PEPTIDE
<222> LOCATION: (9)
<223> OTHER INFORMATION: Lys(BOC)
<220> FEATURE:
<221> NAME/KEY: PEPTIDE
<222> LOCATION: (12)
<223> OTHER INFORMATION: Gln(Trt)
<220> FEATURE:
<221> NAME/KEY: PEPTIDE
<222> LOCATION: (13)
<223> OTHER INFORMATION: Asp(OtBu)
<220> FEATURE:
<221> NAME/KEY: PEPTIDE
<222> LOCATION: (14)
<223> OTHER INFORMATION: "This C-terminal amino acid is bonded via an
      amide bond to Rink Amide MBHA resin."

<400> SEQUENCE: 29

Lys Glu Arg Val Asp Trp Leu Arg Lys Leu Leu Gln Asp Val
 1               5                  10

<210> SEQ ID NO 30
<211> LENGTH: 19
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Lys(BOC)
<220> FEATURE:
<221> NAME/KEY: PEPTIDE
<222> LOCATION: (2)
<223> OTHER INFORMATION: His(Trt)
<220> FEATURE:
<221> NAME/KEY: PEPTIDE
<222> LOCATION: (4)
<223> OTHER INFORMATION: Asn(Trt)
<220> FEATURE:
<221> NAME/KEY: PEPTIDE
<222> LOCATION: (5)
<223> OTHER INFORMATION: Ser(OtBu)
<220> FEATURE:
<221> NAME/KEY: PEPTIDE
<222> LOCATION: (6)..(10)
<223> OTHER INFORMATION: "Synthetic Peptide: The side chains of Lys at
      position 6 and Asp at position 10 are linked by an
```

```
      amide bond."
<220> FEATURE:
<221> NAME/KEY: PEPTIDE
<222> LOCATION: (7)
<223> OTHER INFORMATION: Glu(OtBu)
<220> FEATURE:
<221> NAME/KEY: PEPTIDE
<222> LOCATION: (8)
<223> OTHER INFORMATION: Arg(PMC)
<220> FEATURE:
<221> NAME/KEY: PEPTIDE
<222> LOCATION: (6)..(10)
<223> OTHER INFORMATION: "Synthetic Peptide: The side chains of Lys at
      position 6 and Asp at position 10 are linked by an
      amide bond."
<220> FEATURE:
<221> NAME/KEY: PEPTIDE
<222> LOCATION: (11)
<223> OTHER INFORMATION: Trp(BOC)
<220> FEATURE:
<221> NAME/KEY: PEPTIDE
<222> LOCATION: (13)
<223> OTHER INFORMATION: Arg(PMC)
<220> FEATURE:
<221> NAME/KEY: PEPTIDE
<222> LOCATION: (14)
<223> OTHER INFORMATION: Lys(BOC)
<220> FEATURE:
<221> NAME/KEY: PEPTIDE
<222> LOCATION: (17)
<223> OTHER INFORMATION: Gln(Trt)
<220> FEATURE:
<221> NAME/KEY: PEPTIDE
<222> LOCATION: (18)
<223> OTHER INFORMATION: Asp(OtBu)
<220> FEATURE:
<221> NAME/KEY: PEPTIDE
<222> LOCATION: (6)..(10)
<223> OTHER INFORMATION: "Synthetic Peptide: The side chains of Lys at
      position 6 and Asp at position 10 are linked by an
      amide bond."

<400> SEQUENCE: 30

Lys His Leu Asn Ser Lys Glu Arg Val Asp Trp Leu Arg Lys Leu Leu
  1               5                  10                  15

Gln Asp Val

<210> SEQ ID NO 31
<211> LENGTH: 12
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Ala
<220> FEATURE:
<221> NAME/KEY: PEPTIDE
<222> LOCATION: (3)
<223> OTHER INFORMATION: Ser(OtBu)
<220> FEATURE:
<221> NAME/KEY: PEPTIDE
<222> LOCATION: (4)
<223> OTHER INFORMATION: Glu(OtBu)
<220> FEATURE:
<221> NAME/KEY: PEPTIDE
<222> LOCATION: (6)
<223> OTHER INFORMATION: Gln(Trt)
<220> FEATURE:
<221> NAME/KEY: PEPTIDE
<222> LOCATION: (9)
<223> OTHER INFORMATION: His(Trt)
<220> FEATURE:
<221> NAME/KEY: PEPTIDE
<222> LOCATION: (10)
<223> OTHER INFORMATION: Asn(Trt)
<220> FEATURE:
```

```
<221> NAME/KEY: MOD_RES
<222> LOCATION: (8)
<223> OTHER INFORMATION: Nle

<400> SEQUENCE: 31

Ala Val Ser Glu Ile Gln Leu Xaa His Asn Leu Gly
 1               5                   10

<210> SEQ ID NO 32
<211> LENGTH: 31
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Ala
<220> FEATURE:
<221> NAME/KEY: PEPTIDE
<222> LOCATION: (3)
<223> OTHER INFORMATION: Ser(OtBu)
<220> FEATURE:
<221> NAME/KEY: PEPTIDE
<222> LOCATION: (4)
<223> OTHER INFORMATION: Glu(OtBu)
<220> FEATURE:
<221> NAME/KEY: PEPTIDE
<222> LOCATION: (6)
<223> OTHER INFORMATION: Gln(Trt)
<220> FEATURE:
<221> NAME/KEY: PEPTIDE
<222> LOCATION: (9)
<223> OTHER INFORMATION: His(Trt)
<220> FEATURE:
<221> NAME/KEY: PEPTIDE
<222> LOCATION: (10)
<223> OTHER INFORMATION: Asn(Trt)
<220> FEATURE:
<221> NAME/KEY: PEPTIDE
<222> LOCATION: (13)
<223> OTHER INFORMATION: Lys(BOC)
<220> FEATURE:
<221> NAME/KEY: PEPTIDE
<222> LOCATION: (14)
<223> OTHER INFORMATION: His(Trt)
<220> FEATURE:
<221> NAME/KEY: PEPTIDE
<222> LOCATION: (16)
<223> OTHER INFORMATION: Asn(Trt)
<220> FEATURE:
<221> NAME/KEY: PEPTIDE
<222> LOCATION: (17)
<223> OTHER INFORMATION: Ser(OtBu)
<220> FEATURE:
<221> NAME/KEY: PEPTIDE
<222> LOCATION: (18)..(22)
<223> OTHER INFORMATION: "Synthetic Peptide: The side chains of Lys at
      position 18 and Asp at position 22 are linked by
      an amide bond."
<220> FEATURE:
<221> NAME/KEY: PEPTIDE
<222> LOCATION: (19)
<223> OTHER INFORMATION: Glu(PtBu)
<220> FEATURE:
<221> NAME/KEY: PEPTIDE
<222> LOCATION: (20)
<223> OTHER INFORMATION: Arg(PMC)
<220> FEATURE:
<221> NAME/KEY: PEPTIDE
<222> LOCATION: (22)..(30)
<223> OTHER INFORMATION: "Synthetic Peptide: The side chains of Lys at
      position 13 and Asp at position 30 are linked by
      an amide bond."
<220> FEATURE:
<221> NAME/KEY: PEPTIDE
<222> LOCATION: (23)
<223> OTHER INFORMATION: Trp(BOC)
<220> FEATURE:
```

```
<221> NAME/KEY: PEPTIDE
<222> LOCATION: (25)
<223> OTHER INFORMATION: Arg(PMC)
<220> FEATURE:
<221> NAME/KEY: PEPTIDE
<222> LOCATION: (26)
<223> OTHER INFORMATION: Lys(BOC)
<220> FEATURE:
<221> NAME/KEY: PEPTIDE
<222> LOCATION: (29)
<223> OTHER INFORMATION: Gln(Trt)
<220> FEATURE:
<221> NAME/KEY: PEPTIDE
<222> LOCATION: (18)
<223> OTHER INFORMATION: Asp(OtBu)
<220> FEATURE:
<221> NAME/KEY: PEPTIDE
<222> LOCATION: (30)
<223> OTHER INFORMATION: "This C-terminal amino acid is bonded via an
      amide bond to Rink Amide MBHA resin."
<220> FEATURE:
<221> NAME/KEY: MOD_RES
<222> LOCATION: (8)
<223> OTHER INFORMATION: X =  Norleucine; Nle

<400> SEQUENCE: 32

Ala Val Ser Glu Ile Gln Leu Xaa His Asn Leu Gly Lys His Leu Asn
 1               5                  10                  15

Ser Lys Glu Arg Val Asp Trp Leu Arg Lys Leu Leu Gln Asp Val
            20                  25                  30

<210> SEQ ID NO 33
<211> LENGTH: 2
<212> TYPE: PRT
<213> ORGANISM: Artificial Sequence
<220> FEATURE:
<221> NAME/KEY: PEPTIDE
<222> LOCATION: (2)
<223> OTHER INFORMATION: Asp(OAllyl)
<220> FEATURE:
<221> NAME/KEY: PEPTIDE
<222> LOCATION: (1)
<223> OTHER INFORMATION: BOC-Val
<220> FEATURE:
<221> NAME/KEY: PEPTIDE
<222> LOCATION: (2)
<223> OTHER INFORMATION: "This C-terminal amino acid is in the form of
      an ester with benzyl alcohol."

<400> SEQUENCE: 33

Val Asp
 1

<210> SEQ ID NO 34
<211> LENGTH: 2
<212> TYPE: PRT
<213> ORGANISM: Artificial Sequence
<220> FEATURE:
<221> NAME/KEY: PEPTIDE
<222> LOCATION: (1)
<223> OTHER INFORMATION: "The N-terminus is in the form of a
      hydrochloride salt."
<220> FEATURE:
<221> NAME/KEY: PEPTIDE
<222> LOCATION: (2)
<223> OTHER INFORMATION: Asp(OAllyl)
<220> FEATURE:
<221> NAME/KEY: PEPTIDE
<222> LOCATION: (2)
<223> OTHER INFORMATION: "This C-terminal acid is in the form of an
      ester with benzyl alcohol."

<400> SEQUENCE: 34
```

```
Val Asp
 1

<210> SEQ ID NO 35
<211> LENGTH: 3
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Arg(PMC)
<220> FEATURE:
<221> NAME/KEY: PEPTIDE
<222> LOCATION: (3)
<223> OTHER INFORMATION: Asp(OAllyl)
<220> FEATURE:
<221> NAME/KEY: PEPTIDE
<222> LOCATION: (3)
<223> OTHER INFORMATION: "This C-terminal amino acid is in the form of
      an ester with benzyl alcohol."

<400> SEQUENCE: 35

Arg Val Asp
 1

<210> SEQ ID NO 36
<211> LENGTH: 3
<212> TYPE: PRT
<213> ORGANISM: Unknown
<220> FEATURE:
<221> NAME/KEY: PEPTIDE
<222> LOCATION: (1)
<223> OTHER INFORMATION: Arg(PMC)
<220> FEATURE:
<221> NAME/KEY: PEPTIDE
<222> LOCATION: (3)
<223> OTHER INFORMATION: Asp(OAllyl)
<220> FEATURE:
<221> NAME/KEY: PEPTIDE
<222> LOCATION: (3)
<223> OTHER INFORMATION: "This C-terminal amino acid is in the form of
      an ester with benzyl alcohol."

<400> SEQUENCE: 36

Arg Val Asp
 1

<210> SEQ ID NO 37
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Glu(OtBu)
<220> FEATURE:
<221> NAME/KEY: PEPTIDE
<222> LOCATION: (2)
<223> OTHER INFORMATION: Arg(PMC)
<220> FEATURE:
<221> NAME/KEY: PEPTIDE
<222> LOCATION: (4)
<223> OTHER INFORMATION: Asp(OAllyl)
<220> FEATURE:
<221> NAME/KEY: PEPTIDE
<222> LOCATION: (4)
<223> OTHER INFORMATION: "This C-terminal amino acid is in the form of
      an ester with benzyl alcohol."

<400> SEQUENCE: 37

Glu Arg Val Asp
 1
```

```
<210> SEQ ID NO 38
<211> LENGTH: 4
<212> TYPE: PRT
<213> ORGANISM: Artificial Sequence
<220> FEATURE:
<221> NAME/KEY: PEPTIDE
<222> LOCATION: (1)
<223> OTHER INFORMATION: Glu(OtBu)
<220> FEATURE:
<221> NAME/KEY: PEPTIDE
<222> LOCATION: (2)
<223> OTHER INFORMATION: Arg(PMC)
<220> FEATURE:
<221> NAME/KEY: PEPTIDE
<222> LOCATION: (4)
<223> OTHER INFORMATION: Asp(OAllyl)
<220> FEATURE:
<221> NAME/KEY: PEPTIDE
<222> LOCATION: (4)
<223> OTHER INFORMATION: "This C-terminal amino acid is in the form of
      an ester with benzyl alcohol."

<400> SEQUENCE: 38

Glu Arg Val Asp
  1

<210> SEQ ID NO 39
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Lys(Alloc)
<220> FEATURE:
<221> NAME/KEY: PEPTIDE
<222> LOCATION: (2)
<223> OTHER INFORMATION: Glu(OtBu)
<220> FEATURE:
<221> NAME/KEY: PEPTIDE
<222> LOCATION: (3)
<223> OTHER INFORMATION: Arg(PMC)
<220> FEATURE:
<221> NAME/KEY: PEPTIDE
<222> LOCATION: (5)
<223> OTHER INFORMATION: Asp(OAllyl)
<220> FEATURE:
<221> NAME/KEY: PEPTIDE
<222> LOCATION: (5)
<223> OTHER INFORMATION: "This C-terminal amino acid is in the form of
      an ester with benzyl alcohol."

<400> SEQUENCE: 39

Lys Glu Arg Val Asp
  1               5

<210> SEQ ID NO 40
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Lys
<220> FEATURE:
<221> NAME/KEY: PEPTIDE
<222> LOCATION: (2)
<223> OTHER INFORMATION: Glu(OtBu)
<220> FEATURE:
<221> NAME/KEY: PEPTIDE
<222> LOCATION: (3)
<223> OTHER INFORMATION: Arg(PMC)
<220> FEATURE:
<221> NAME/KEY: PEPTIDE
```

```
<222> LOCATION: (5)
<223> OTHER INFORMATION: "This C-terminal amino acid is in the form of
      an ester with benzyl alcohol."

<400> SEQUENCE: 40

Lys Glu Arg Val Asp
 1               5

<210> SEQ ID NO 41
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Lys
<220> FEATURE:
<221> NAME/KEY: PEPTIDE
<222> LOCATION: (1)..(5)
<223> OTHER INFORMATION: "Synthetic Peptides: The side chains of Lys at
      position 1 and Asp at position 5 are linked by an
      amide bond."
<220> FEATURE:
<221> NAME/KEY: PEPTIDE
<222> LOCATION: (2)
<223> OTHER INFORMATION: Glu(OtBu)
<220> FEATURE:
<221> NAME/KEY: PEPTIDE
<222> LOCATION: (3)
<223> OTHER INFORMATION: Arg(PMC)
<220> FEATURE:
<221> NAME/KEY: PEPTIDE
<222> LOCATION: (1)
<223> OTHER INFORMATION: "Synthetic Peptides: The side chains of Lys at
      position 1 and Asp and position 5 are linked by an
      amide bond."
<220> FEATURE:
<221> NAME/KEY: PEPTIDE
<222> LOCATION: (5)
<223> OTHER INFORMATION: "This C-terminal amino acid is in the form of
      an ester with benzyl alcohol."

<400> SEQUENCE: 41

Lys Glu Arg Val Asp
 1               5

<210> SEQ ID NO 42
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Lys
<220> FEATURE:
<221> NAME/KEY: PEPTIDE
<222> LOCATION: (1)..(5)
<223> OTHER INFORMATION: "Synthetic Peptide: The side chains of Lys at
      position 1 and Asp at position 5 arelinked by an
      amide bond."
<220> FEATURE:
<221> NAME/KEY: PEPTIDE
<222> LOCATION: (2)
<223> OTHER INFORMATION: Glu(OtBu)
<220> FEATURE:
<221> NAME/KEY: PEPTIDE
<222> LOCATION: (3)
<223> OTHER INFORMATION: Arg(PMC)
<220> FEATURE:
<221> NAME/KEY: PEPTIDE
<222> LOCATION: (5)
<223> OTHER INFORMATION: "Synthetic Peptide: The side chains of Lys at
      position 1 and Asp at position 5 are linked by an
      amide bond."
```

```
<400> SEQUENCE: 42

Lys Glu Arg Val Asp
 1               5

<210> SEQ ID NO 43
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Lys(Alloc)
<220> FEATURE:
<221> NAME/KEY: PEPTIDE
<222> LOCATION: (2)
<223> OTHER INFORMATION: Glu(OtBu)
<220> FEATURE:
<221> NAME/KEY: PEPTIDE
<222> LOCATION: (3)
<223> OTHER INFORMATION: Arg(PMC)
<220> FEATURE:
<221> NAME/KEY: PEPTIDE
<222> LOCATION: (5)
<223> OTHER INFORMATION: Asp(OAllyl)
<220> FEATURE:
<221> NAME/KEY: PEPTIDE
<222> LOCATION: (5)
<223> OTHER INFORMATION: "The C-terminus Asp is bonded to chlorotrityl
      resin."

<400> SEQUENCE: 43

Lys Glu Arg Val Asp
 1               5

<210> SEQ ID NO 44
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Lys
<220> FEATURE:
<221> NAME/KEY: PEPTIDE
<222> LOCATION: (2)
<223> OTHER INFORMATION: Glu(OtBu)
<220> FEATURE:
<221> NAME/KEY: PEPTIDE
<222> LOCATION: (3)
<223> OTHER INFORMATION: Arg(PMC)
<220> FEATURE:
<221> NAME/KEY: PEPTIDE
<222> LOCATION: (5)
<223> OTHER INFORMATION: "The C-terminus Asp is bonded to chlorotrityl
      resin."

<400> SEQUENCE: 44

Lys Glu Arg Val Asp
 1               5

<210> SEQ ID NO 45
<211> LENGTH: 5
<212> TYPE: PRT
<213> ORGANISM: Artificial Sequence
<220> FEATURE:
<221> NAME/KEY: PEPTIDE
<222> LOCATION: (1)
<223> OTHER INFORMATION: FMOC-Lys
<220> FEATURE:
<221> NAME/KEY: PEPTIDE
<222> LOCATION: (1)
<223> OTHER INFORMATION: "The C-terminus Asp is bonded to chlorotrityl
      resin."
```

```
<220> FEATURE:
<221> NAME/KEY: PEPTIDE
<222> LOCATION: (2)
<223> OTHER INFORMATION: Glu(OtBu)
<220> FEATURE:
<221> NAME/KEY: PEPTIDE
<222> LOCATION: (3)
<223> OTHER INFORMATION: Arg(PMC)
<220> FEATURE:
<221> NAME/KEY: PEPTIDE
<222> LOCATION: (5)
<223> OTHER INFORMATION: "The C-terminus Asp is bonded to chlorotrityl
      resin."
<220> FEATURE:
<221> NAME/KEY: PEPTIDE
<222> LOCATION: (1)..(5)
<223> OTHER INFORMATION: The side chains of Lys at position 1 and Asp at
      position 5 are linked by an amide bond.

<400> SEQUENCE: 45

Lys Glu Arg Val Asp
  1               5

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence:HPTH
      Analogue
<220> FEATURE:
<221> NAME/KEY: PEPTIDE
<222> LOCATION: (1)
<223> OTHER INFORMATION: Product=Ala
<220> FEATURE:
<221> NAME/KEY: MOD_RES
<222> LOCATION: (8)
<223> OTHER INFORMATION: Xaa =  Norleucine (Nle)
<220> FEATURE:
<221> NAME/KEY: PEPTIDE
<222> LOCATION: (18)
<223> OTHER INFORMATION: Product = Lys
<220> FEATURE:
<221> NAME/KEY: PEPTIDE
<222> LOCATION: (18)
<223> OTHER INFORMATION: The side chain of Lys is bonded by an amide
      bridge to the side chain of Asp.
<220> FEATURE:
<221> NAME/KEY: PEPTIDE
<222> LOCATION: (22)
<223> OTHER INFORMATION: Product = Asp
<220> FEATURE:
<221> NAME/KEY: PEPTIDE
<222> LOCATION: (22)
<223> OTHER INFORMATION: The side chain of Asp is bonded by an amide
      bridge to the side chain of Lys.
<220> FEATURE:
<221> NAME/KEY: PEPTIDE
<222> LOCATION: (26)
<223> OTHER INFORMATION: Product = Lys
<220> FEATURE:
<221> NAME/KEY: PEPTIDE
<222> LOCATION: (26)
<223> OTHER INFORMATION: The side chain of Lys is bonded by an amide
      bridge to the side chain of Asp.
<220> FEATURE:
<221> NAME/KEY: PEPTIDE
<222> LOCATION: (27)
<223> OTHER INFORMATION: Product = Leu
<220> FEATURE:
<221> NAME/KEY: PEPTIDE
<222> LOCATION: (30)
<223> OTHER INFORMATION: Product = Asp
<220> FEATURE:
<221> NAME/KEY: PEPTIDE
<222> LOCATION: (30)
```

-continued

<223> OTHER INFORMATION: The side chain of Asp is bonded by an amide
     bridge to the side chain of Lys.

<400> SEQUENCE: 46

```
Ala Val Ser Glu Ile Gln Leu Xaa His Asn Leu Gly Lys His Leu Asn
 1               5                  10                  15

Ser Lys Glu Arg Val Asp Trp Leu Arg Lys Leu Leu Gln Asp Val His
            20                  25                  30

Asn Phe
```